(12) United States Patent
Palczewski et al.

(10) Patent No.: US 8,962,691 B2
(45) Date of Patent: Feb. 24, 2015

(54) RETINOID REPLACEMENTS AND OPSIN AGONISTS AND METHODS FOR THE USE THEREOF

(75) Inventors: Krzysztof Palczewski, Bay Village, OH (US); David A. Saperstein, Seattle, WA (US)

(73) Assignee: University of Washington, Seattle, WA (US)

( * ) Notice: Subject to any disclaimer, the term of this patent is extended or adjusted under 35 U.S.C. 154(b) by 143 days.

(21) Appl. No.: 13/619,607

(22) Filed: Sep. 14, 2012

(65) Prior Publication Data

US 2013/0072568 A1    Mar. 21, 2013

Related U.S. Application Data

(63) Continuation of application No. 13/420,465, filed on Mar. 14, 2012, which is a continuation of application No. 10/548,612, filed as application No. PCT/US2004/007937 on Mar. 15, 2004, now abandoned.

(60) Provisional application No. 60/455,182, filed on Mar. 14, 2003.

(51) Int. Cl.
| | |
|---|---|
| *A61K 31/11* | (2006.01) |
| *A61K 31/07* | (2006.01) |
| *A61K 38/17* | (2006.01) |
| *A61K 31/382* | (2006.01) |
| *A61K 31/435* | (2006.01) |
| *A61K 31/695* | (2006.01) |

(52) U.S. Cl.
CPC ............. *A61K 31/07* (2013.01); *A61K 38/1709* (2013.01); *A61K 31/11* (2013.01); *A61K 31/382* (2013.01); *A61K 31/435* (2013.01); *A61K 31/695* (2013.01); *Y10S 514/912* (2013.01)
USPC .......................................... 514/703; 514/912

(58) Field of Classification Search
USPC ................................... 514/703, 912
See application file for complete search history.

(56) References Cited

U.S. PATENT DOCUMENTS

| | | | |
|---|---|---|---|
| 3,196,078 | A | 7/1965 | Chatzinoff et al. |
| 3,517,067 | A | 6/1970 | Stern |
| 5,457,135 | A | 10/1995 | Baranowitz et al. |
| 5,620,970 | A | 4/1997 | Han et al. |
| 5,837,728 | A | 11/1998 | Purcell |
| 5,869,468 | A | 2/1999 | Freeman |
| 6,300,328 | B1 | 10/2001 | Klimko |
| 6,552,009 | B2 | 4/2003 | Achkar |
| 6,696,069 | B2 | 2/2004 | Harichian et al. |
| 7,951,841 | B2 | 5/2011 | Palczewski et al. |
| 8,324,270 | B2 | 12/2012 | Maeda et al. |
| 2002/0028849 | A1 | 3/2002 | Godkin et al. |
| 2003/0215413 | A1 | 11/2003 | Fares et al. |
| 2003/0228277 | A1 | 12/2003 | Gehlsen |
| 2004/0022766 | A1 | 2/2004 | Acland et al. |
| 2004/0097587 | A1 | 5/2004 | Arbiser |
| 2006/0167088 | A1 | 7/2006 | Widder et al. |
| 2006/0281821 | A1 | 12/2006 | Palczewski et al. |
| 2008/0275133 | A1 | 11/2008 | Schwartz et al. |
| 2011/0034554 | A1 | 2/2011 | Washington |
| 2011/0288170 | A1 | 11/2011 | Palczewski et al. |
| 2012/0041073 | A1 | 2/2012 | Palczewski et al. |
| 2012/0322891 | A1 | 12/2012 | Palczewski et al. |
| 2013/0072443 | A1 | 3/2013 | Palczewski et al. |
| 2013/0072556 | A1 | 3/2013 | Palczewski et al. |
| 2013/0072557 | A1 | 3/2013 | Maeda et al. |
| 2013/0072558 | A1 | 3/2013 | Maeda et al. |
| 2013/0072559 | A1 | 3/2013 | Palczewski et al. |
| 2013/0072560 | A1 | 3/2013 | Palczewski et al. |
| 2013/0072561 | A1 | 3/2013 | Maeda et al. |
| 2013/0072568 | A1 | 3/2013 | Palczewski et al. |
| 2013/0072569 | A1 | 3/2013 | Palczewski et al. |
| 2013/0079403 | A1 | 3/2013 | Palczewski et al. |
| 2013/0196950 | A1 | 8/2013 | Palczewski et al. |

FOREIGN PATENT DOCUMENTS

| | | |
|---|---|---|
| CA | 2601278 A1 | 9/2005 |
| CN | 1169854 A | 1/1998 |
| CN | 1455780 A | 11/2003 |
| CN | 198898 A | 6/2007 |
| EP | 0803248 A2 | 10/1997 |
| GB | 1449027 | 9/1976 |
| GB | 1526410 A | 9/1978 |
| JP | 61-275266 A | 5/1986 |
| JP | 6340525 A | 12/1994 |
| JP | 8198746 A | 8/1996 |
| RU | 2106843 C1 | 3/1998 |
| WO | WO 96/24344 | 8/1996 |
| WO | WO 99/09969 | 3/1999 |
| WO | WO 99/29315 A | 6/1999 |
| WO | WO 00/68364 A2 | 11/2000 |
| WO | WO 02/055540 A1 | 7/2002 |
| WO | WO 02/082904 A2 | 10/2002 |
| WO | WO 03/059336 A1 | 7/2003 |
| WO | WO 2004/082622 A2 | 9/2004 |

(Continued)

OTHER PUBLICATIONS

Travis et al., Diseases caused by defects in the visual cycle: retinoids as potential therapeutic agents, Annu Rev Pharmacol Toxicol. 2007;47:469-512.*

(Continued)

*Primary Examiner* — Gigi Huang

(74) *Attorney, Agent, or Firm* — Jacqueline F. Mahoney; Judy M. Mohr; McDermott Will & Emery LLP

(57) ABSTRACT

Compositions of and methods for using synthetic retinoids as retinoid replacements and opsin agonists are provided.

6 Claims, 8 Drawing Sheets

(56) References Cited

FOREIGN PATENT DOCUMENTS

| WO | WO 2005/079774 A2 | 9/2005 |
|---|---|---|
| WO | WO 2006/002097 A2 | 1/2006 |
| WO | WO 2006/033734 A2 | 3/2006 |

OTHER PUBLICATIONS

Maeda et al., QLT091001, a 9-cis-retinal analog, is well-tolerated by retinas of mice with impaired visual cycles, Invest Ophthalmol Vis Sci. Jan. 17, 2013;54(1):455-66.*
Koenekoop et al., Oral 9-cis retinoid for childhood blindness due to Leber congenital amaurosis caused by RPE65 or LRAT mutations: an open-label phase 1b trial, Lancet. Jul. 11, 2014 pii: S0140-6736(14)60153-7, printed from http://www.ncbi.nlm.nih.gov/pubmed/25030840, abstract only, 2 pages.*
Ames et al., "Biomedical studies on vitamin A. XIV. Biopetencies of Geometric Isomers of Vitamin in the Rat", J. Am. Chem. Soc., vol. 77. pp. 4134-4136 (1955).
Chan et al., "Delayed dark adaptation caused by nilutamide", J. Neuro-Opthalmology, vol. 28, No. 4, pp. 158-159 (2008).
Gaffney et al., "Aging and cone dark adaptation", Optom. Vis. Sci., vol. 89, No. 8, pp. 1219-1224 (2012).
Marmor et al., "Abipunctate retinopathy with cone dysfunction and no abnormality in RDH5 or RLBP1 genes", Retina, vol. 23, No. 4, pp. 543-546 (2003).
Maugard et al., "Synthesis of water-soluble retinol derivatives by enzymatic method", Biotechnol. Prog. vol. 18, pp. 424-428 (2002).
Morimura et al., "Mutations in the RPE65 gene in patients with autosomal recessive retinitis pigmentosa or Leber congenital amaurosis", PNAS USA, vol. 95, pp. 3088-3093 (1998).
Remington: The Science and Practice of Pharmacy, 19$^{th}$ Edition, Gennaro et al., Ed., Mack Publishing Company, pp. 1528-1529 (1995).
Huttunen et al., "Prodrugs—from Serendipity to Rational Design", Pharmacological Reviews, vol. 63, No. 3, pp. 750-771 (2011).
Newton et al., "Structure-Activity Relationships of Retinoids in Hamster Tracheal Organ Culture", Cancer Res., vol. 40, pp. 3413-3425 (1980).
Perusek and Maeda, "Vitamin A Derivatives as Treatment Options for Retinal Degenerative Disease", Nutrients, vol. 5, pp. 2646-2666 (2013).
Ablonczy et al., "11-cis-retinyl reduces constitutive phosphorylyzation and improves quantum catch in retinoid-deficient mouse rod photoreceptors", J. Biol. Chem., vol. 277, pp. 40491-40498 (2002).
Acland et al., "Gene therapy restores vision in a canine model of childhood blindness", Nature Genetics, vol. 28, pp. 92-95 (2001).
Acland et al., "Long-term restoration of rod and cone vision by single dose rAAV-mediated gene transfer to the retina in a canine model of childhood blindness", Mol. Ther., vol. 12, No. 6, pp. 1072-1082 (2005).
Aggarwal et al., "2-Halogeno-1,3-dithiane 1,3-dioxide: a diastereoselective carbonyl anion equivalent in reactions with aldehydes", J. Chem. Soc., vol. 1, pp. 11-19 (1997).
Albeck et al., "Factors Affecting the Absorption Maxima of Acidic Forms of Bacteriorhodopsin", Biophys. J., vol. 56, pp. 1259-1265 (1989).
Aleman et al., "Impairment of the transient papillary light reflex in Rpe65(-/-) mice and humans with leber congenital amaurosis", Invest. Opthalmol. Vis Sci., vol. 45, No. 4, pp. 1259-1271 (2004).
Asato et al., "Fluorinated modopsin analogues from 10-flouro- and 14-flouroretinal", J. Am. Chem. Soc., vol. 100, No. 18, pp. 5957-5960 (1978).
Baehr et al., "The retinoid cycle and retina disease", Vision Research, vol. 43, pp. 2957-2958 (2003).
Batten et al., "Lecithin-retinol acyltransferase is essential for accumulation of all-trans-retinyl esters in the eye and in the liver" The Journal of Biological Chemistry, vol. 279, No. 11, pp. 10422-10432 (2004).
Batten et al., "Pharmacological and rAAV gene therapy rescue of visual functions in a blind mouse model of leber congenital amaurosis", PLoS Medicine, vol. 2, Issue 11, No. e333, pp. 1177-1189 (2005).
Beischel et al., "Azidotetrafluorophenyl retinal analogue: synthesis and bacteriorhodopsin pigment formation", Photochemistry and Photobiology, vol. 60, No. 1, pp. 64-68 (1994).
Bernstein et al., "Biochemical characterization of the retinoid isomerasa system of the eye", J. Biol. Chem., vol. 262, No. 35, pp. 16848-16857 (1987).
Berson et al., "A randomized trial of vitamin A and vitamin E supplementation for retinitis Pigmentosa", Arch. Opthamol., vol. 111, pp. 761-772 (1993).
Berson et al., "Retinitis pigmentosa: unfolding its mystery", Proc. Natl. Sci. USA, vol. 93, pp. 4526-4528 (1996).
Berson, "Treatment of retinitis Pigmentosa with vitamin A", Digital J. Opthamol., vol. 4, No. 7 Massachusetts Eye and Ear Infirmary, Harvard Medical School (1998).
Berson et al., "Disease progression in patients with dominant retinitis pigmentosa and rhodopsin mutations", Invest. Opthalmol. Vis. Sci., vol. 43, No. 9, pp. 3027-3036 (2002).
Biesalski et al, "Sensitive Analysis of Retinyl Esters by Isocratic Adsorption Chromatography", J. Clin. Chem. Biochem., vol. 27, No. 2, pp. 65-74 (1989) Abstract only.
Birnbach et al., "Retinoic acid accelerates photoreceptor cell death by apoptosis in Pro23HIS rhodopsin transgenic mice". Invest. Opthalmol. Vis. Sci., vol. 38, No. 4, pp. s311 (1997).
Boehm et al., "Photoaffinity labeling studies of bacteriorhodopsin with [15-$^3$h]-3-Diazo-4-keto-all-trans-retinal", J. Am. Chem. Soc., vol. 112, pp. 7779-7782 (1990).
Borhan et al., "Chemoenzymatic synthesis of 1-cis-retinal photoaffinity analog by use of squid retinochrome", J. Am. Chem. Soc., vol. 119, pp. 5758-5759 (1997).
Borhan et al., "Efficient synthesis of 11-cis-retinoids", Chem. Eur. J., vol. 5, No. 4, pp. 1172-1175 (1999).
Bridges, "Vitamin A* and the Role of the Pigment Epithelimn during Bleaching and Regeneration of Rhodopsin in the Frog Eye", Exp. Eye Res., vol. 22, pp. 435-455 (1976).
Buczylko et al., "Mechanisms of opsin activation", J. Biol. Chem., vol. 271, No. 34, pp. 20621-20630 (1996).
Caldwell et al., "Synthesis of retinals with eight- and nine-membered rings in the side chain. models for rhodopsin photobleaching intermediates", J. Org. Chem., vol. 58, pp. 3533-3537 (1993).
Capecchi "Altering the genome by homologous recombination", Science, vol. 244, No. 4910, pp. 1288-1292 (1989).
Carney and Russell, "Correlation of Dark Adaptation Test Results with Serum Vitamin A Levels in Diseased Adults", J. Nutr., vol. 110, pp. 552-557 (1980).
Caruso et al., "Effects of fenretinide (4-HPR) on dark adaptation", XP002475887; STN Database Accession No. 1998:418096 & Archives of Ophthalmology (Chicago), vol. 116, No. 6, pp. 759-763, CODEN: AROPAW; ISSN:0003-9950, (1998) Abstract only.
Chapple et al., "Looking at protein misfolding neurodegenerative disease through retinitis pigmentosa", ACNR, vol. 3, Issue 1, pp. 12-13 (2003).
Chatzinoff et al., "Eleven-cis vitamin A in the treatment of retinitis Pigmentosa", Arch. Opthalmol., vol. 80, pp. 417-419 (1968).
Cideciyan et al., "Rod and cone visual cycle consequences of a null mutation in the 11-cis-retinol dehydrogenase gene in man", Vis. Neurosci., vol. 17, No. 5. pp. 667-678 (2000).
Colmenares et al., "11,12-Difluororhodopsin and related odd-numbered fluororhodopsins. the use of $J_{F,F}$ for following a cis-trans isomerization process", J. Am. Chem. Soc., vol. 121, pp. 5803-5804 (1999).
Congdon et al., "Responsiveness of dark-adaptation threshold to vitamin A and β-carotene supplementation in pregnant and lactating women in Nepal", Am. J. Clin. Nutr., vol. 72, pp. 1004-1009 (2000).
Corson et al., "Sensitization of bleach rod photoreceptors by 11-cis-locked analogues retinal", PNAS USA, vol. 87, pp. 6823-6827 (1990).
Crescitelli and Pearlman, "Can isorhodopsin be produced in the living rat?", Vision Res., vol. 13, pp. 2515-2525 (1973).

(56) References Cited

OTHER PUBLICATIONS

Crescitelli et al., "The spectral properties and photosensitivies of analogue photopigments regenerated with 10- and 14-substituted retinal analogues" Proc. R. Soc. Lond. B, vol. 233, pp. 55-76 (1988).
Crouch et al., "Photo sensitive pigments formed with rat opsin", Investigative Opthalmology, vol. 15, No. 10, pp. 872-875 (1976).
Crouch and Katz, "The effect of retinal isomers on the ver and erg of vitamin A deprived rats", Vision Res., vol. 31, pp. 109-115 (1980).
Crouch et al., "Inhibition of rhodopsin regeneration of cyclohexyl derivatives", Vision Research, vol. 22, No, 12, pp. 1451-1456 (1982).
Crouch et al., "Opsin pigments formed with acyclic retinal analogues", FEBS, vol. 158, No. 1, pp. 139-142 (1983).
Crouch et al., "Cycloheptatrienylidene analog of 11-cis retinal", Invest. Opthalmol. Vis. Sci., vol. 25, pp. 419-418 (1984).
Crouch, "Yearly review: studies of rhodopsin and bacteriorhodopsin using modified retinals", Photochemistry and Photobiology, vol. 44, No. 6, pp. 803-807 (1986).
De Grip et al., "10 20 methanorhodopsins 7e 9e 13e-10 20 mthanorhodopsin and 7e 9z 13z-10 20 methanorhodopsin 11-cis-locked rhodopsin analog pigments with unusual thermal and photostability", Eur. J. Biochem., vol. 191, No. 1, pp. 211-220 (1990).
Delange et al., "An additional methyl group at the 10-position of retinal dramatically slows down the kinetics of the rhodopsin photocascade", Biochemistry, vol. 37, No. 5, pp. 1411-1420 (1998).
Drachev et al., "An investigation of the electrochemical cycle of bacteriorhodopsin analogs with the modified ring", Arch. Biochem. Biophys., vol. 270, No. 1, pp. 184-197 (1989).
Driessen et al., "Disruption of the 11-cis-retinol dehydrogenase gene leads to accumulation of cis-retinols and cis-retinyl esters", Mol. Cell Biol., vol. 20, No. 12, pp. 4275-4287 (2000).
Ebrey et al., "Properties of several sterically modified retinal analogs and their photosensitive pigments", Biochemistry, vol. 14, No. 18, pp. 3933-3941 (1975).
Eyring et al., "Assignment and interpretation of hydrogen out-of-plane vibrations in the resonance raman spectra of rhodopsin and bathorhodopsin", Biochemistry, vol. 21, pp. 384-393 (1982).
European Search Report From related European Application No. EP 04757476, mailed on Jun. 5, 2008.
European Search Report From Related European Patent Application No. EP 1154402, search completed on Sep. 5, 2011.
European Search Report From Related European Patent Application No. EP 1154404, search completed on Sep. 6, 2011.
European Search Report From Related European Patent Application No. EP 1154534, search completed on Sep. 5, 2011.
Fan et al., "Isorhodopsin rather than rhodopsin mediates rod function in RPE65 knock-out mice", PNAS, vol. 100, No. 23, pp. 13662-13667 (2003).
Fujimoto et al., "On the bioactive conformation of the rhodopsin chromophore: absolute sense of twist around the 6-s-cis bond", Chem. Eur. J., vol. 7, No. 19, pp. 4198-4204 (2001).
Fujimoto et al., "Solution and biologically relevant conformations of enantiomeric 11-cis-locked cyclopropyl retinals", J. Am. Chem. Soc., vol. 124, pp. 7294-7302 (2002).
Fukada et al., "Studies on structure and function of rhodopsin by use of cyclopentatrienylidene 11-cis-locked rhodopsin". Biochemistry, vol. 23, No. 24, pp. 5826-5832 (1984).
Futterman et al., "The composition of liver vitamin A ester and the synthesis of vitamin A ester by liver microsomes", J. Biol. Chem., vol. 239, No. 12, pp. 4077-4080 (1964).
Gao and Hollyfield, "Aging of the human retina" Inv. Opth. Vis. Sci., vol. 33, pp. 1-17 (1992).
Gartner et al., "Quantum yield of chapso-solubilized rhodopsin and 3-hydroxy retinal containing bovine opsin", Photochemistry and Photobiology, vol. 54, No. 6, pp. 1047-1055 (1991).
Geroski et al., "Drug delivery for posterior segment eye disease", IOVS, vol. 41, No. 5, pp. 961-964 (2000).
Grant et al., "Treatable forms of retinitis pigmentosa associated with systemic neurological disorders", Int. Opthalmol. Clin., vol. 41, No. 1, (2001) printed from http://www.ncbi.nim.nih.gov/pubmed/11198137 on Jan. 14, 2009 Abstract only.
Haeseleer et al., "Dual-substrate specificity short chain retinol dehydrogenases from the vertebrate retina", J. Biol. Chem., vol. 277, No. 47, pp. 45537-45546 (2002).
Haig et al., "Vitamin A and Rod-Cone Dark Adaption in Cirrhoses of the Liver", Science, vol. 87, No. 2267, pp. 534-536 (1938).
Han et al., "The C9 methyl group of retinal interacts with glycine-121 in rhodopsin", PNAS, vol. 94, pp. 13442-13447 (1997).
Harvard Health Publications, "The aging eye: preventing and treating eye disease", Harvard Helath Publications, 3 pgs. (2011) printed from http://www.health.harvard.edu/special_health_reports/the_Aging_Eye on Nov. 5, 2011.
Head, "Natural therapies for ocular disorders, part one: diseases of the retina", Alt. Med. Review, vol. 4, No. 5, pp. 342-359 (1999).
Hiraki et al., "Bacteriorhodopsin analog regenerated with 13-desmethyl-13-lodoretinal", Biophysical Journal, vol. 83, pp. 3460-3469 (2002).
Hirano et al., "Constraints of opsin structure on the ligand-binding site: studies with ring-fused retinals", Photochemistry and Photobiology, vol. 76, No. 6, pp. 606-615 (2002).
Hisatomi et al., "Critical role of photoreceptor apoptosis in functional damage after retinal detachment", Curr. Eye Res , vol. 24, No. 3, 161-172 (2002) Abstract only, 1 pg., printed from http://www.ncbi.nim.nih.gov/pubmed/12221523.
Hu et al., "Unbleachable rhodopsin with an 11-cis-locked eight-membered ring retinal: the visual transduction process", Biochemistry, vol. 33, pp. 408-416 (1994).
Illing et al., "A Rhodopsin mutant linked to autosomal dominant retinitis pigmentosa is prone to aggregate and interacts with ubiquitin proteasome system", J. Biol. Chem., vol. 277, No. 37, pp. 34150-34160 (2002).
Imai et al., "Probing for the threshold energy for visual transduction: red-shifted visual pigment analogs from 3-methoxy-3-dehydroretinal and related compounds". Photochemistry and Photobiology, vol. 70, No. 1, pp. 111-115 (1999).
Imamoto et al., "Structure around $C_6$-$C_7$ bond of the chromophore in bathorhodopsin: low-temperature spectroscopy of 6s-cis-locked bicyclic rhodopsin analogs", Biochemistry, vol. 35, pp. 6257-6262 (1996).
Imanishi et al., "Noninvase two-photon imaging reveals retinyl ester storage structures in the eye", Cell Biol. vol. 164, pp. 373-383 (2004).
International Search Report from related PCT Patent Application No. PCT/US2004/007987 mailed on Dec. 3, 2004, application now published as International Publication No. WO2004/082622, published on Sep. 30, 2004.
International Search Report from related PCT Patent Application No. PCT/US2005/021812 mailed on Dec. 28, 2005, application now published as International Publication No. WO2006/002097 , published on Jan. 5, 2006.
International Search Report from related PCT Patent Application No. PCT/US2009/000824 mailed on Nov. 5, 2009, application now published as International Publication No. WO2009/102418, published on Aug. 20, 2009.
Jackson et al., "Aging and scotopic sensitivity", Vis. Res., vol. 38, pp. 3655-3662 (1998).
Jackson et al., "Aging and dark adaption", Vis. Res. vol. 39, pp. 3975-3982 (1999).
Jackson et al.. "Photoreceptor degeneration and dysfunction in aging and age-related maculopathy", Aging Res. Rev., vol. 1, No. 3, pp. 381-396 (2002).
Jacobson et al., "Retinal degenerations with truncation mutations in the cone-rod homeobox (CRX) gene", Invest. Opthalmol. Vis. Sci., vol. 39, No. 12, pp. 2417-2426 (1988).
Jacobson et al., "Night blindness in Sorsby' fundus dystrophy reversed by vitamin A" Nat. Genet. vol. 11, pp. 27-32 (1995).
Jacobson et al., "Phenotypic Marker for Early Disease Detection in Dominant Late-Onset Retinal Degeneration", IOVS, vol. 42, No. 8, pp. 1882-1890 (2001).
Jacobson et al., "Identifying photoreceptors in blind eyes caused RPE65 mutations: Prerequisite for human gene therapy success", PNAS USA, vol. 102, No. 17, pp. 6177-6182 (2005).

(56) References Cited

OTHER PUBLICATIONS

Jang, "Mechanism of rhodopsin activation as examined with ring-constrained retinal analogs and the crystal structure of the ground state protein", The Journal of Biological Chemistry, vol. 276, No. 28, pp. 26148-26153 (2001).

Jang et al., "Characterization of a dehydrogenase activity responsible for oxidation of 11-cis-retinal in the retinal pigment epithelium of mice with a disrupted RDH5 gene. A model for the human heredity disease fundus albunctatus", J. Biol. Chem., vol. 276, No. 35, pp. 32456-32465 (2001).

Karnaukhova et al., "Bioactivity of visual pigments with sterically modified retinal analogs", Bioorganic Chemistry, Vol 27, pp. 372-382 (1999).

Kirillova et al., "Cyclopentene and cyclohexene retinal analogs react differently with bacterioopsin", Chemical Abstracts, vol. 120, pp. 557, (1994). Abstract No. 128:187138 Abstract only.

Kubo et al., "Effect of vitamin A palmitate on vitamin A-deficient rabbits", XP002475885; STN Database Accession No. 2000:172779 & Nippon Ganka Gakkai Zasshi, vol. 103, No. 10, pp. 729-733 CODEN:NGZAA6; ISSN: 0029-0203,1999 Abstract only.

Kuksa et al., "Biochemical and physiological properties of rhodopsin regenerated with 11-cis-6-ring- and 7-ring-retinals", The Journal of Biological Chemistry, vol. 277, No. 44, pp. 42315-42324 (2002).

Lamb and Pugh, "Dark adaption and the retinoid cycle of vision", Prog. Retin. Eye Res., vol. 23, pp. 307-380 (2004).

Lewin et al., "Synthesis and characterization of trans-, 13-cis-, and 11-cis, 13-cis-12-(hydroxymethyl)retinols", J. Org. Chem., vol. 49, pp. 649-652 (1984).

Li et al., "Effect of vitamin A supplementation on rhodopsin mutants threonine-17→methionine and proline-347→serine in transgenic mice and in cell cultures", Proc. Natl. Acad. Sci. USA, vol. 95, pp. 11933-11938 (1998).

Li et al., "Delivery of 9-cis retinal of photoreceptors from bovine serum albumin", Photochem. Photobiol., vol. 69, No. 4, pp. 500-504 (1999).

Lin et al., "Vibrational Assignment of Torsional Normal Modes of Rhodopsin: Probing Excited-State Isomerization Dynamics along the Reaction $C_{11}$-$C_{12}$ Torsion Coordinate", J. Phys. Chem. B, vol. 102, pp. 2787-2806 (1998).

Liu et al., "The nature of restriction in the binding site of rhodopsin. A model study", J. Am. Chem. Soc., vol. 106, No. 26, pp. 8298-8300 (1984).

Maeda et al., "Evaluation of the role of the retinal g protein-coupled receptor (RGR) in the vertebrate retina in vivo". Journal of Neurochemistry, vol. 85, pp. 944-956 (2003).

Maeda et al, "Improvement in Rod and Cone Function in Mouse Model of *Fundus albipunctatus* after Phannacologic Treatment with 9-*cis*-Retinal", IOVS, vol. 47, No. 10, pp. 4540-4546 (2006).

Maeda et al., "Effects of long-term administration of 9-cis-retinyl acetate on visual function in mice", Inv. Opth. Vis. Sci., vol. 50, No. 1, pp. 322-332 (2009).

Massoud et al., "Plasma vitamin A and beta-carotene in retinitis pigmentosa", Brit. J. Opthal., vol. 59, pp. 200-204 (1975).

Maugard et al., "Enzymatic synthesis of derivatives of vitamin A in organic media", J. Mol. Cat. B, vol. 8, pp. 275-280 (2000).

Mata et al., "Substrate specificity of retinyl ester hydrolase activity in retinal pigment epithelium", Journal of Lipid Research, vol. 39, pp. 604-612 (1998).

Matsukawa et al., "Role of purpurin as a retinal-binding protein in goldfish retina during the early stage of optic nerve regeneration: Its priming action on neurite outgrowth", J. Neurosci., vol. 24, No. 38, pp. 8346-8353 (2004).

Maxwell et al., "Photodynamic responses in rhodotorula glutinis in the absence of added sensitizers", Photochemistry and Photobiology, vol. 13, No. 3, pp. 259-273 (1971).

Mayo Clinic, "Retinal detachment", 8 pgs (2010) printed from http://www.mayoclinic.com/health/retinal-detachment/DS00254/METHOD=print&DSECTION=all.

McBee et al. "Confronting complexity: the interlink of phototransduction and retinoid metabolism in the vertebrate retina", Prog. Ret Eye Res., vol. 20, No. 4, pp. 469-529 (2001).

MedlinePlus, "Diabetic retinopathy", 5 pgs. (2011) printed from http://www.nim.nih.gov/medlineplus/ency/articie/00212.htm.

Mizukami et al., "Photoisomerization mechanism of the rhodopsin chromophore: picosecond photolysis of pigment containing 11-cis-locked eight-membered ring retinal", PNAS vol. 90, pp. 4072-4076 (1993).

Nakamura et al., "A high association with cone dystrophy in fundus albipunctatus caused by mutations of the RDH5 gene", Invest. Opthalmol. Vis. Sci., vol. 41, No. 12, pp. 3925-3932 (2000).

Nishiguchi et al., "A novel mutation (I143NT) in guanylate cyclase-activating protein 1 (GCAP1) associated with autosomal dominant cone degeneration", Invest. Opthalmol. Vis. Sci., vol. 45, No. 11, pp. 3863-3870 (2004).

Noell, "Suitability of retinol, retinal and retinyl palmitate for the regeneration of bleached rhodopsin in the isolated frog retina", XP002486105, STN Database Accession No. 1985: 164043 & Vision Research, vol. 24, No. 11, pp. 1615-1622, CODEN:VISRAM; ISSN:0042-6989, (1984) Abstract only.

Noorwez et al., "Pharmacological chaperone-mediated in vivo folding and stabilization of the P23H-opsin mutant associated with autosomal dominant retinitis Pigmentosa", J. Biol. Chem., vol. 278, No. 16, pp. 14442-14450 (2003).

Noorwez et al., "Retinoids assist the cellular folding of the autosomal dominant retinitis Pigmentosa opsin mutant P23H", J. Biol. Chem., vol. 279, No. 16, pp. 16278-16284 (2004).

Norum and Blomhoff, "McCollum Award Lecture, 1992: Vitamin A absorption, transport, cellular uptake, and storage", Am. J. Clin. Nutr., vol. 56, pp. 735-744 (1992).

O'Byrne et al., "Retinoid adsorption and storage is impaired in mice lacking lecithin: retinol acyltransferase (LRAT)", J. Biol. Chem., vol. 280, pp. 35647-35657 (2005).

Owsley et al., "Delays in rod-mediated dark adaption in early age-related maculopathy", Ophthalmology, vol. 108, pp. 1196-1202 (2001).

Owsley et al., "Effect of short-term, high-dose retinol on dark adaption in agingand early age-related maculopathy", Invest. Opthalmol. Vis. Sci., vol. 47, No. 4, pp. 1310-1318 (2006).

Paik et al., "9-cis-retinoids: biosynthesis of 9-cis-retinoic acid", Biochemistry, vol. 39, No. 27, pp. 8073-8084 (Jul. 2000) Abstract only.

Parry et al., "Visual pigment reconstitution in intact goldfish retina using synthetic retinaldehyde isomers", Vision research, vol. 40. No. 17, pp. 2241-2247 (2000).

Radomska et al., "The use of some ingredients for microemulsion preparation containing retinol and its esters", XP002475886, STN Database Accession No. 2000:139945 & International Journal of Pharmaceutics, vol. 196, No. 2, pp. 131-134 CODEN:IJPHDEI; ISSN; 0378-5173, (2000). Abstract only.

Rao et al., "Isomers of 3 7 11 trimethyldodeca-2 4 6 8 10-pentaenal A linear analog of retinal and lower homologues in their interaction with bovine opsin and bacterioopsin", Photochemistry and Photobiology, vol. 41, No. 2, pp. 171-174 (1985).

Rao et al., "5-(Trifluoromethyl)bacteriorhodopsin does not translocate protons", J. Am. Chem. Soc., vol. 108, pp. 6077-6078 (1986).

Rao et al., "Regioselective photo isomerisation of retinolacetate" Tetrahedron Letters, vol. 31, No. 24, pp. 3441-3444 (1990).

Redmond et al., "Rpe65 is necessary for production of 11-cis-vitamin A in the retinal visual cycle", Nature Genetics, vol. 20, pp. 344-351 (1998).

Reid et al., "Mass Spectral Analysis of Eleven Analogs of Vitamin A1", Lipids, vol. 8, No. 1, pp. 558-565 (1973).

Renk, "A rhodopsin pigment containing a spin-lapeled retinal" J. Am. Soc., vol. 109, pp. 6163-6168 (1987).

Rezabek et al., "Effects of dietary retinyl acetate on the promotion of hepatic enzyme-altered foci by polybrominated biphenyls in initiated rats", Food Chem. Toxicol., vol. 27, No. 8, pp. 539-544 (1989) Abstract only.

Robinson et al., "Opsins with mutations at the site of chromophore attachment constitutively activate transducin but are not

(56) References Cited

OTHER PUBLICATIONS phosphorylated by rhodopsin kinase", Proc. Natl. Acad. Sci. USA, vol. 91, No. 12, pp. 5411-5415 (1994).
Rotenstreich et al., "Treatment of retinal dystrophy, fundus albipunctatus, with oral 9-cis-b-carotene", Br. J. Opthalmol., vol. 94, pp. 616-621 (2010).
Russell, "The vitamin A spectrum: from deficiency to toxicity", Am. J. Clin. Nutr., vol. 71, pp. 878-884 (2000).
Saliba et al., "The celluar fat of mutant rhodopsin: quality control, degradation and aggresome formation", J. Cell Science, vol. 115, pp. 2907-2918 (2002).
Sandberg et al., "Clinical expression correlates with location of rhodopsin mutation in dominant retinitis Pigmentosa", Invest. Opthalmol. Vis. Sci. vol. 36, No. 9, pp. 1934-1942 (1995).
Sekiya et al., "Effect of modification of the chromophore in retinochrome", Biophysical Chemistry, vol. 56, pp. 31-39 (1995).
Semenova et al., "Systems for delivery of vitamin A to the retina in retinitis pigmentosa", XP002475884; STN Database Accession No. 2002:438129 & New Insights Into Retinal Degenerative Diseases, [Proceedings of the International Symposium on Retinal Degeneration], 9th, Durango, Co, United States, (2000), Meeting Date (2000), pp. 105-110, Editor (Anderson & Lavail), (2001) Abstract only.
Semenova et al., "Stabilization of all-trans-retinol by cyclodextrins: a comparative study using HPLC and fluorescence spectroscopy", XP002475883; STN Database Accession No. 2003:494986 & Journal of Inclusion Phenomena and Macrocyclic Chemistry, Volume Date (2002), vol. 44, No. 1-4, pp. 155-158 CODEN:JIPCF5; ISSN:1388-3127, (2003) Abstract only.
Semple-Rowland et al., "A null mutation in the photoreceptor guanylate cyclase gene causes the retinal degeneration chicken phenotype", Proc. Natl. Acad. Sci. USA, vol. 95, No. 3, pp. 1271-1276 (1998).
Sen et al., "Synthesis and binding studies of a photoaffinity label for bovine rhodopsin", J. Am. Chem. Soc., vol. 104, pp. 3214-3216 (1982).
Sibulesky et al., "Safety of<7500 RE (<25000 IU) vitamin A daily in adults with retinitis Pigmentosa". Am. J. Clin. Nutr., vol. 69 pp. 656-663 (1999).
Sokal et al., "GCAP1 (Y99C) mutant is constitutively active in autosomal dominant cone dystophy", Mol. Cell. vol. 2, No. 1, pp. 129-133 (1998).
Spaeth, "Ophthalmic Surgery: Principles & Practice, Second Edition", Harcourt Brace Jovanich Inc., pp. 85-99 (1990).
Stecher et al., "Preferential release of *11-cis-retinol* from retinal pigment epithelial cells in the presence of cellular retinaldehyde-binding protein" The Journal of Biological Chemistry, vol. 274, No. 13, pp. 8577-8585 (1999).
Steinberg et al., "Isomer composition and spectra of the dark and light adapted forms of artificial bacteriorhodopsins", Photochemistry and Photobiology, vol. 54, No. 6, pp. 969-976 (1991).
Supplementary European Search Report From Related European Patent Application No. EP 04757476, mailed on Jun. 5, 2008.
Supplementary European Search Report From Related European Patent Application No. EP 05773576, mailed on Aug. 4, 2008.
Tan et al., "Absolute sense of twist of the C12-C13 bond of the retinal chromophorein bovine rhodopsin based on exciton-coupled CD spectra 11, 12-dihydroretinal analogues", Agnew. Chem. Int. Ed. Engl. vol. 36, No. 19, pp. 2089-2093 (1997).
Tarkhov et al , "Study of a structure-property relationship for retinal derivatives taking into account their conformational flexibility", Chemical Abstracts, vol. 128, No. 18, pp. 270 (1998) Abstract No. 128:214600 Abstract only.
Teller et al., "Advances in determination of a high-resolution three-dimensional structure of rhodopsin, a model of G-protein-coupled receptors (GPCRs)", Biochemistry vol. 40, No. 26, pp. 7761-7772 (2001).
The Eye Digest, "Aging eye in the US", 2 pgs. (2011) printed from http://web.archive.org/web/20060810014820/http://www.agingeye.net/mainnews/usaging.php.
Thomson Scientific, London, GB; AN 1995-063773, XP002475888 & JP 06340525 A (Lion Corp); Dec. 13, 1993 Abstract only.
Thomson Scientific, London, GB; AN 1996-408307, XP002475889 & JP 08198746 A (Lion Corp); Aug. 6, 1996 Abstract only.
Thomson Scientific, London, GB; AN 1998-518867, XP002475890 & RU 2106843 C1 (Krasy Med Acad); Mar. 20, 1998 Abstract only.
Thompson et al., "Mutations in the gene encoding lecithin retinol acyltransferase are associated with early-onset severe retinal dystrophy". Nat. Genet. vol. 28, pp. 123-124 (2001).
Thompson et al., "Gene defects in vitamin A metabolism of the retinal pigment epithelium", Genetics in Ophthalmology, vol. 37, pp. 141-154 (2003).
Travis et al., "Diseases caused by defects in the visual cycle: retinoids as potential therapeutic agents", Annu. Rev. Pharmacol. Toxicol., vol. 47, pp. 469-512 (2007).
Van Hooser et al., "Rapid restoration of visual pigment and function with oral retinoid in a mouse model of childhood blindness", PNAS, vol. 97, No. 15, pp. 8623-8628 (2000).
Van Hooser et al., "Recovery of visual functions in a mouse model of leber congenital amaurosis", The Journal of Biological Chemistry, vol. 277, No. 21, pp. 19173-19182 (2002).
Vitamin Converter, copy of known vitamin A conversion, 3 pgs., printed from http://www.robert-forbes.com/resources/vitaminconverter.html on Apr. 19, 2012.
Wada et al., "Retinoids and related compounds. part 26. synthesis of (11Z)-8,18- propano- and methano-retinals and conformational study of the rhodopsin chromophore", J. Chem. Soc., vol. 1, pp. 2430-2439 (2001).
Weiser and Somorjai, "Bioactivity of cis and dicis isomers of vitamin A esters", Internatl. J. Vit. Nutr., vol. 62, pp. 201-208 (1992).
Wingerath et al., "Analysis of cyclic and acyclic analogs of retinol, retinoic acid, and retinal by laser desorption Ionization-, matrix-assisted laser desorption ionization-mass spectrometry, and UV/Vis spectroscopy", Analytical Biochemistry, vol. 272, pp. 232-242 (1999).
Witovsky et al., "Formation, conversion, and utilization of isorhodopsin, rhodopsin, and porphyropsin by rod photoreceptors in the xenopus retina", J. Gen. Physiol., vol. 72, pp. 821-836 (1978).
www.wrongdiagnosis.com, "Symptom: night blindness", pp. 1-13 (Jun. 3, 2008).
Woodward et al., "The inflow and outflow of anti-glaucoma frugs", Trends Pharm. Sci., vol. 25, Issue 5, pp. 238-241 (2004).
Yamamoto et al., "Important role of the proline residue in the signal sequence that directs the secretion of humam lysozyme in *Saccharomyces cerevisiae*", Biochemistry, vol. 28, pp. 2728-2732.
Yamamoto et al., "Mutations in the gene encoding 11-cis retinol dehydrogenase cause delayed dark adaptation and fundus Albipunctatus", Nat. Genet., vol. 22, No. 2, pp. 188-191 (1999).
Yan et al., "Mechanism of activation of sensory rhodopsin I: evidence for a steric trigger", PNAS, vol. 88, pp. 9412-9416 (1991).
Yoshikami et al., "Visual pigments of vitamin A-deficient rat following vitamin A2 administration", Vision Research, vol. 9, No. 6, pp. 633-636 (1969).
Yoshizawa and Wald, "Photochemistry of lodopsin", Nature vol. 214, pp. 566-571 (1967).
Zankel et al., "Bovine rhodopsin with 11-cis-locked retinal chromophore neither activates rhodopsin kinase nor undergoes conformational change upon irradiation", J. American Chemical Soc., vol. 112, No. 13, pp. 5387-5388 (1990).
Zhang et al., "Structure, alternative splicing, and expression of the human RGS9 gene", Gene, vol. 240, No. 1, pp. 23-24 (1999).
Zhu et al., "A naturally occurring mutation of the opsin gene (T4R) in dogs affects glycosylation and stability of the G protein-coupled receptor", J. Biol. Chem., vol. 279, No. 51, pp. 53828-53839 (2004).
Ohgane et al., "Retinobenzaldehydes as proper-trafficking inducers of folding-defective p23H rhodopsin mutant responsible for retinitis pigmentosa", Bioorg. Med. Chem., vol. 18, No. 19, pp. 7022-7028 (2010).
Chen et al., "Inherent instability of the retinitis pigmentosa P23H mutant opsin", JBC Papers in Press, Manuscript M114.551713, 31 pages, Latest version can be accessed at http://www.jbc.org/cgi/doi/10.1074/jbc.M114.551713, Published Feb. 10, 2014.

(56) References Cited

OTHER PUBLICATIONS

Mendes et al., "Pharmacological manipulation of rhodopsin retinitis pigmentosa", Advances in Experimental Medicine and Biology, Chapter 36, pp. 317-323, DOI 10.1007/978-1-4419-1399-9_36, Springer Science+Business Media, LLC (2010).

Price et al., "Mislocation and degradation of human P23H-Rhodopsin-GFP in a knockin mouse model of retinitis pigmentosa", Inv. Opth. Vis. Sci., vol. 52, No. 13, pp. 9728-9736 (2011).

Sakami et al., "Probing mechanisms of photoreceptor degeneration in a new mouse model of the common form of autosomal dominant retinitis pigmentosa due to P23H opsin mutations", JBC Papers in Press, Manuscript M110.209759, 29 pages, Latest version can be accessed at http://www.jbc.org/cgi/doi/10.1074/jbc.M110.209759, Published Jan. 11, 2011.

Dorwald, *Side Reactions in Organic Synthesis: A Guide to Succesful Synthesis Design*, Wiley-VCH Verlag GmbH & Co. KGaA, Weinheim, Preface p. IX, (2005).

Howard et al., "Coparative distribution, pharmacokinetics and placental permeabilities of all-trans-retinoic acid, 13-cis-retinoic acid, all-trans-4-oxo-retinoic acid, retinyl acetate and 9-cis-retinal in hamsters", Arch. Toxicol., vol. 63, pp. 112-120 (1989).

Jang et al., "Characterization of a dehydrogenase activity responsible for oxidation of 11-cis-retinol in the retinal pigment epithelium of mice with a disrupted RDH5 gene. A model for the human heredity disease fundus albunctatus", J. Biol. Chem., vol. 276, No. 35, pp. 32456-32465 (2001).

Jin et al., "Noncovalent occupancy of the retinal-binding pocket of opsin diminishes bleaching adaption of retinal cones", Neuron, No. 11, pp. 513-522 (1993).

Karnaukhova et al., "Bioactivity of visual pigments with sterically modified retinal analogs", Bioorganic Chemistry, vol. 27, pp. 372-382 (1999).

Kefalov et al., "Role of nocovalent binding of 11-cis-retinal to opsin in dark adaption of rod and cone photoreceptors", Neuron, vol. 29, Issue 3, pp. 749-755 (2001).

Kemp et al., "Visual Function and Rhodopsin Levels in Humans with Vitamin A Deficiency", Exp. Eye Res., vol. 46, pp. 185-197 (1988).

Kirillova et al., "Cyclopentene and cyclohexene retinal analogs react differently with bacterioopsin", Chemical Abstracts, vol. 120, pp. 557, (1994) Abstract No. 128:187138 Abstract only.

Kubo et al, "Effect of vitamin A palmitate on vitamin A-deficient rabbits", XP002475885; STN Database Accession No. 2000:172779 & Nippon Ganka Gakkai Zasshi, vol. 103, No. 10, pp. 729-733 CODEN:NGZAA6; ISSN: 0029-0203;1999 Abstract only.

Kuksa et al., "Biochemical and physiological properties of rhodopsin regenerated with 11-cis-6-ring-and 7-ring-retinals", The Journal of Biological Chemistry, vol. 277, No. 44, pp. 42315-42324 (2002).

Kuksa et al., "Retinoid cycle in the vertebrate retina: experimental approaches and mechanisms of isomerization", Vision Research, vol. 43, pp. 2959-2981 (2003).

Kupfer et al., "Information for doctors who follow patients with retinitis pigmentosa", National Eye Institute (1993), printed from http://www.nei.nih.gov/news/clinicalalerts/alert-rp.asp on Jan. 15, 2009, 2 pages.

Lamb and Pugh, "Dark adaptation and the retinoid cycle of vision", Prog. Retin. Eye Res., vol. 23, pp. 307-380 (2004).

Lamb and Pugh, "Phototransduction, Dark Adaptation, and Rhodopsin Regeneration", IOVS, vol. 47, No. 12, pp. 5138-5152 (2006).

Lang, "Ocular drug delivery conventional ocular formulations", Adv. Drug Del. Rev., vol. 16, No. 1, pp. 39-43 (1995).

Lawson et al., "Retinal analog restoration of photophobic responses in a blind chlamydomonas-reinhardtll mutant evidence for an archaebacterial like chromophore in a eukaryotic rhodopsin", Biophysical Journal, vol. 60, No. 6, pp. 1490-1498 (1991).

Lewin et al., "Synthesis and characterization of trans-, 13-cis-, and 11-cis, 13-cis-12-(hydroxymethyl)retinois", J. Org. Chem., vol. 49, pp. 649-652 (1984).

Lewis et al., "Steric barrier to bathorhodopsin decay in 5-demethyl and mesityl analogues of rhodopsin", J. Am. Chem. Soc., vol. 123, pp. 10024-10029 (2001).

Li et al.,"Effect of vitamin A supplementation on rhodopsin mutants threonie-17→methionine and proline-347→serine in transgenic mice and in cell cultures", Proc. Natl. Acad. Sci. USA, vol. 95, pp. 11933-11938 (1998).

Li et al., "Delivery of 9-cis retinal to photoreceptors from bovine serum albumin", Photochem. Photobiol., vol. 69, No. 4, pp. 500-504 (1999).

* cited by examiner

| Compound | Isomer | Non-bleached sample in solution | | | | Bleached sample in solution | | | | Non-bleached sample in rhodopsin | | | | Bleached sample in rhodopsin | | | | RDH (pmol/min) | |
|---|---|---|---|---|---|---|---|---|---|---|---|---|---|---|---|---|---|---|---|
| | | 1 | 2 | 3 | 4 | 1 | 2 | 3 | 4 | 1 | 2 | 3 | 4 | 1 | 2 | 3 | 4 | all-trans | 11-cis |
| 1 | 9,11,13-tricis- | 98 | 0 | 2 | 0 | 49 | 1 | 14 | 36 | 30 | - | 6* | 64 | 27 | - | 47* | 26 | 0.45 | 2.97 |
| 2 | 11,13-dicis- | 0 | 100 | 0 | 0 | 4 | 42 | 47 | 7 | 0 | 12 | 88 | 0 | 0 | 14 | 86 | 0 | 1.24 | 0.07 |
| 3 | 11-cis- | 0 | 0 | 100 | 0 | 2 | 22 | 68 | 8 | 0 | 5 | 95 | 0 | 0 | 6 | 94 | 0 | 0.57 | 0.03 |
| 4 | 9,11-dicis- | 0 | 0 | 0 | 100 | 18 | - | 22* | 60 | 19 | - | 18* | 73 | 19 | - | 41* | 40 | 1.28 | 0.01 |
FIG. 4A
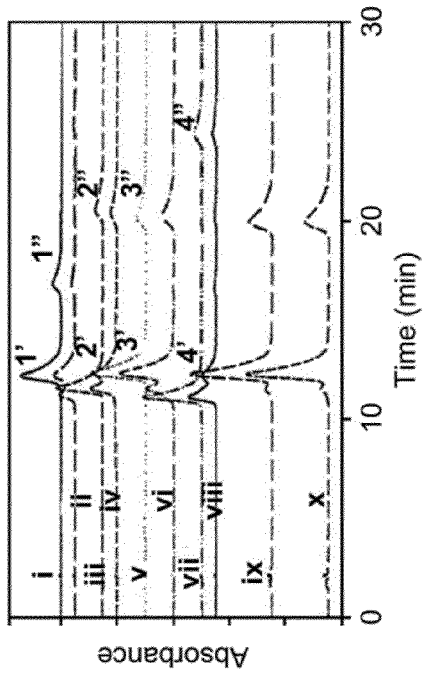
FIG. 4C
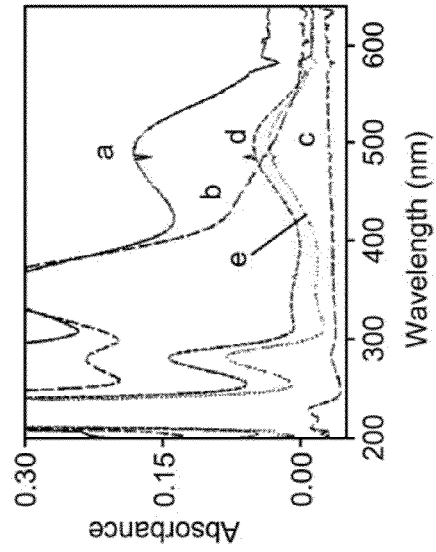
FIG. 4B

RETINOID REPLACEMENTS AND OPSIN AGONISTS AND METHODS FOR THE USE THEREOF

CROSS-REFERENCES TO RELATED APPLICATIONS

This application is a continuation of U.S. application Ser. No. 13/420,465, filed Mar. 14, 2012, pending, which is a continuation of U.S. application Ser. No. 10/548,612, filed Sep. 7, 2005, abandoned, which is a U.S. National Phase Application under 35 U.S.C. §371 of International Application No. PCT/US2004/007937, filed Mar. 15, 2004, which claims the benefit of U.S. Provisional Patent Application No. 60/455,182, filed Mar. 14, 2003. The disclosure of each of the priority documents is incorporated by reference herein.

STATEMENT AS TO RIGHTS TO INVENTIONS MADE UNDER FEDERALLY SPONSORED RESEARCH OR DEVELOPMENT

This invention was made with government support under EY008061 and EY009339 awarded by the National Institutes of Health. The government has certain rights in this invention.

BACKGROUND OF THE INVENTION

A diminished visual acuity or total loss of vision may result from a number of eye diseases or disorders caused by dysfunction of tissues or structures in the anterior region of the eye and/or posterior region of the eye. The eye is divided anatomically into an anterior and posterior segment. The anterior segment includes the cornea, anterior chamber, iris and ciliary body (anterior choroid), posterior chamber and crystalline lens. The posterior segment includes the retina with optic nerve, choroid (posterior choroid) and vitreous. The posterior portion of the eyeball supports the retina, choroid and associated tissues.

Examples of eye disorders resulting from the pathologic conditions of structures in the anterior segment of the eye are dry eye syndrome, keratitis or corneal dystrophy, cataracts, and glaucoma. Disease or disorders of the posterior segment of the eye in general are retinal or choroidal vascular diseases or hereditary diseases such as Leber Congenital Amaurosis. Age related macular degeneration (AMD) is one of the specific diseases associated with the posterior portion of the eyeball and is the leading cause of blindness among older people. AMD results in damage to the macula, a small circular area in the center of the retina. Because the macula is the area which enables one to discern small details and to read or drive, its deterioration may bring about diminished visual acuity and even and to read or drive, its deterioration may bring about diminished visual acuity and even blindness. The retina contains two forms of light receiving cells, rods and cones, that change light into electrical signals. The brain then converts these signals into the images. The macula is rich in cone cells, which provides central vision. People with AMD suffer deterioration of central vision but usually retain peripheral sight.

There are several types of AMD. The "dry" (non-exudative) type accounts for about 90% of AMD cases. The "wet" (exudative) form afflicts only about 10% of AMD patients. However, the wet form is a more serious disease than the dry form and is responsible for about 90% of the instances of profound visual loss resulting from the disease. Wet AMD often starts abruptly with the development of tiny, abnormal, leaky blood vessels termed CNVs (chorodial new vessels), directly under the macula. In most patients, this leads to scarring and severe central vision loss, including distortion, blind spots, and functional blindness.

Signs of AMD such as drusen, which are abnormal yellow deposits under the retina, can be present even in patient with normal vision. Drusen look like specks of yellowish material under the retina. They are deposits of extracellular material that accumulate between retinal pigment epithelium (RPE) and Bruch's Membrane. The RPE is a specialized cell layer that ingests used-up outer tips of the rod and cone cells and provides them with essential nutrients (e.g., vitamin A derivatives). Brach's membrane is a noncellular structure (composed mostly of collagen) that separates the RPE from the choroidal circulation below. The choroidal circulation provides blood supply to the rods, cones and RPE cells. A few small drusen normally form in the human eye, usually after age 40. AMD, in contrast, is almost always associated with a build-up of additional drusen. Drusen occur in two forms. Hard drusen are small, solid deposits that apparently do no harm when present in small numbers. Soft drusen are larger and may have indistinct borders. As soft drusen build up between the RPE and Bruch's membrane, they lift up the RPE and force the two layers apart.

Drusen develop long before the abnormal vessels of wet AMD. Three characteristics of soft drusen are risk factors for developing CNV: The presence of five or more drusen deposits; drusen size greater than 63 micrometers (about the thickness of a human hair); and the clumping of the drusen deposits. Some evidence suggests soft drusen are instrumental in the spread of abnormal vessels, but whether they stimulate vessel growth (angiogenesis) or simply provide space for them by lifting up the RPE remains unclear.

Two networks of blood vessels nourish the retina, one located on the retinal surface and the other located deep in the retina, external to Bruch's membrane. The abnormal vessels of AMD originate in the lower network of vessels, called the choroidal circulation. These vessels make their way through Bruch's membrane and spread out under the RPE. Blood and fluids leak from them and cause the photoreceptor cells to degenerate and the macula to detach from the cells under it.

Slightly blurred or distorted vision is the most common early symptom of AMD. Visual loss with dry AMD usually progresses slowly while visual loss with wet AMD proceeds more rapidly and may occur over days or weeks. Patients who have wet AMD in one eye are at increased risk of developing CNVs in the other eye. The magnitude of the risk varies, depending on the appearance of the second eye. The risk is greater in eyes with numerous large drusen, with abnormal pigment changes in the macula, and in patients with a history of high blood pressure.

AMD is now the leading cause of legal blindness in the western world. Reactions that go on in the RPE lead to oxidative products that in turn lead to cell death and neovascularization. This excess metabolism leads to the formation of drusen under the RPE.

Other eye diseases also affect photoreceptor function in the eye. Retinitis Pigmentosa represents disease caused by defects in many different genes. They all have a final common pathway of night blindness and peripheral vision loss that can lead to narrowing of the visual field and eventual loss of all vision in many patients. The rod photoreceptors are usually primarily affected and most of the gene defects leading to the disease occur in genes that are expressed predominantly or only in the rod cells.

One autosomal dominant form of Retinitis Pigmentosa comprises an amino acid substitution in opsin, a proline to histidine substitution at amino acid 23. This defect compromises 10-20% of all Retinitis Pigmentosa cases. This abnormal opsin protein forms a protein aggregate that eventually leads to cell death.

Leber Congenital Amaurosis is a very rare childhood condition that affects children from birth or shortly there after. It affects both rods and cones. There are a few different gene defects that have been associated with the disease. These include the genes encoding the RP65 and LRAT proteins. Both result in a person's inability to make 11-cis-retinal in adequate quantities. In the RP65 defective individuals, retinyl esters build up in the RPE. LRAT-defective individuals are unable to make esters and subsequently secrete any excess retinoids.

Retinitis Punctata Albesciens is another form of Retinitis Pigmentosa that exhibits a shortage of 11-cis-retinal in the rods. Aging also leads to the decrease in night vision and loss of contrast sensitivity due to a shorting of 11-cis-retinal. Excess unbound opsin is believed to randomly excite the visual transduction system. This can create noise in the system, and thus more light and more contrast is necessary to see well.

Congenital Stationary Night Blindness (CSNB) and Fundus Albipunctatus are a group of diseases that are manifested as night blindness, but there is not a progressive loss of vision as in the Retinitis Pigmentosa. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown recently that this is also a progressive disease although much slower than Retinitis Pigmentosa. It is caused by a gene defect that leads to a delay in the cycling of 11-cis-retinal.

Currently, there are few treatments for retinoid deficiency. One treatment, a combination of antioxidant vitamins and zinc, produces only a small restorative effect. Thus, there is a need for compositions and methods of restoring or stabilizing photoreceptor function and ameliorating the effects of deficient levels of endogenous retinoids.

BRIEF SUMMARY OF THE INVENTION

The present invention provides methods of restoring or stabilizing photoreceptor function in a vertebrate visual system. Synthetic retinoids can be administered to human or non-human vertebrate subjects to restore or stabilize photoreceptor function, and/or to ameliorate the effects of a deficiency in retinoid levels.

In one aspect, methods are provided for restoring photoreceptor function in a vertebrate eye. The method generally includes administering to a vertebrate having an endogenous deficiency in the eye an effective amount of a synthetic retinoid in a pharmaceutically acceptable vehicle. The synthetic retinoid binds to opsin in the vertebrate eye and forms a functional opsin/synthetic retinoid complex. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal. The synthetic retinoid can be locally administered to the eye such as, for example, by eye drops, intraocular injection or periocular injection. The synthetic retinoid also can be orally administered to the vertebrate.

In another aspect, a method is provided for sparing the requirement for endogenous retinoid in a vertebrate eye. The method generally includes administering to the eye a synthetic retinoid in a pharmaceutically acceptable vehicle, wherein the synthetic retinoid binds to opsin in the vertebrate eye and forms a functional opsin/synthetic retinoid complex. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal. The endogenous retinoid that is deficient can be, for example, 11-cis-retinal.

In yet another aspect, a method of ameliorating loss of photoreceptor function in a vertebrate eye is provided. The method generally includes prophylactically administering an effective amount of a synthetic retinoid in a pharmaceutically acceptable vehicle to the vertebrate eye. The synthetic binds to opsin protein to form a functional opsin/synthetic retinoid complex. The synthetic retinoid can be, for example, orally administered or locally administered. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal.

In a further aspect, a method of selecting a treatment for a subject having or at risk for developing a diminished visual capacity is provided. The method generally includes determining whether the subject has a deficient endogenous retinoid level, as compared with a standard subject, and administering to the subject an effective amount of a synthetic retinoid in a pharmaceutically acceptable vehicle. The synthetic retinoid binds to opsin in the subject's eye. The subject can be, for example, a human having Leber Congenital Amaurosis, Retinitis Punctata Albesciens, Congenital Stationary Night Blindness, Fundus Albipunctatus or Age-Related Macular Degeneration. In certain embodiments, the endogenous retinoid that is deficient is 11-cis-retinal.

The synthetic retinoid can be, for example, orally or locally administered to a vertebrate, such as by local administration to the vertebrate eye. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal.

In yet further aspects, an ophthalmologic composition is provided that includes a synthetic retinoid in a pharmaceutically acceptable vehicle. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal. The ophthalmologic composition can be, for example, eye drops, an intraocular injectable solution or a periocular injectable solution.

In a further related aspect, an oral dosage form is provided that includes an opsin-binding synthetic retinoid in a pharmaceutically acceptable vehicle. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal.

In another aspect, a method is provided of treating Leber Congenital Amaurosis in a vertebrate subject. The method generally includes administering to the subject an effective amount of a synthetic retinoid in a pharmaceutically acceptable vehicle. The synthetic retinoid binds to opsin in the vertebrate eye and forms a functional opsin/synthetic retinoid complex. The synthetic retinoid can be, for example, a synthetic retinoid of formula I, II, III, IV, V, VI, VII, VIII, IX, X, XI, XII or XIII. In other embodiments, the synthetic retinoid can be, for example, a synthetic retinoid of formula I, II, III, IV, V, VI, VII, VIII, IX, X, XI, XII or XIII, with the proviso that the synthetic retinoid is not 9-cis-retinal. In other embodiments, the synthetic retinoid is 9-cis-retinal.

The synthetic retinoid can be, for example, locally administered to the eye. In certain embodiments, the synthetic retinoid is locally administered by eye drops, intraocular injection, periocular injection, or the like. The synthetic retinoid also can be orally administered to the subject.

In yet another aspect, a method is provided for treating Retinitis Punctata Albesciens. Congenital Stationary Night Blindness or Fundus Albipunctatus in a vertebrate subject. The method generally includes administering to the subject an effective amount of a synthetic retinoid in a pharmaceutically acceptable vehicle. The synthetic retinoid binds to opsin in the vertebrate eye and forms a functional opsin/synthetic retinoid complex. The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal.

The synthetic retinoid can be, for example, locally administered to the eye. The synthetic retinoid can be locally administered by, for example, eye drops, intraocular injection or periocular injection. The synthetic retinoid also can be orally administered to the subject.

In yet a further aspect, a method is provided for treating Age-Related Macular Degeneration in a vertebrate subject. The method generally includes administering to the subject an effective amount of a synthetic retinoid in a pharmaceutically acceptable vehicle. The synthetic retinoid binds to opsin in the vertebrate eye and forms an opsin/synthetic retinoid complex. For example, the synthetic retinoid can bind to free opsin in the eye.

The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal. The synthetic retinoid can be, for example, locally administered to the eye. For example, the synthetic retinoid can be locally administered by eye drops, intraocular injection or periocular injection. The synthetic retinoid also can be orally administered to the subject.

In another aspect, a method is provided of treating or preventing loss of night vision or contrast sensitivity in an aging vertebrate subject. The method generally includes administering to the subject an effective amount of a synthetic retinoid in a pharmaceutically acceptable vehicle. The synthetic retinoid can bind to opsin in the vertebrate eye and form an opsin/synthetic retinoid complex. For example, the synthetic retinoid can bind to free opsin in the eye.

The synthetic retinoid can be, for example, a synthetic retinoid of formula I, II, III, IV, V, VI, VII, VIII, IX, X, XI, XII or XIII. In certain embodiments, the synthetic retinoid is 9-cis-retinal. The synthetic retinoid can be, for example, locally administered to the eye. Suitable methods of local administration include, for example, by eye drops, intraocular injection or periocular injection. The synthetic retinoid also can be orally administered to the subject. In certain embodiments, the synthetic retinoid is administered prophylactically to the subject.

BRIEF DESCRIPTION OF THE DRAWINGS

FIG. 1A, the levels of all-trans-retinyl esters (closed circles) and 11-cis-retinal (closed squares) in Rpe65+/+ compared with levels of all-trans-retinyl esters (open circles) in Rpe65−/− mice as a function of age. FIG. 1B, ester analysis of 9-cis-retinal-treated and untreated Rpe65−/− mice. Rpe65−/− mice were treated with 25 µg of 9-cis-retinal starting at PND 7 every other day until they were 1 month old. Note the y axis scale. FIG. 1C, age-related accumulation of all-trans-retinyl esters in Rpe65−/− mice (gray line with black data points) compared with the ester levels (circles) in animals treated with 9-cis-retinal starting at PND 7 (left panel) (25 µg every other day, and after PND 30 gavaged with 9-cis-retinal (250 µg) once a week) or PND 30 (right panel) gavaged with 9-cis-retinal (250 µg) once a week. The levels of iso-rhodopsin in treated Rpe65−/− mice are indicated by triangles measured as 11-cis-retinyl oximes. FIG. 1D, changes in the RPE-ROS interface in Rpe65 mice treated with 9-cis-retinal. Rpe65−/− mice were treated with 9-cis-retinal (200 µg each) at PND 7, 11, and 15 and analyzed when they were PND 30 (panels c and d) and PND 90 (panels e and f). Rpe65−/− mice were treated with 9-cis-retinal (200 µg each) at PND 30 and analyzed when they were PND 120 (panels g and h). Control retina from untreated Rpe65−/− mice at PND 7 and PND 30 is shown on the top (panels a and b, respectively). Only partially filled lipid-like droplet in early treated mice (left column, arrow in panel c), and considerably improved RPE-ROS processes (right column) in all treated mice were observed. Scale bar, 1 µm.

FIG. 2A, comparison of iso-rhodopsin levels in 1-month-old Rpe65−/− mice gavaged with a single dose of 9-cis-retinal (2.5 mg) and kept under 12 hours light/dark or at constant dark for 37 days (n=4). FIG. 2B, the levels of rhodopsin or iso-rhodopsin in 6-month-old Rpe65−/− mice. The rhodopsin levels in wild-type mice (column a) were compared with iso-rhodopsin in Rpe65−/− mice treated twice with 9-cis-retinal (2.5 mg each time) at 1 month old with 4-day intervals (column c) and treated twice with 3-month (column d) or 4-month (column e) intervals. No rhodopsin iso-rhodopsin was detected in untreated Rpe65−/− mice (column b) (n=4). FIG. 2C, the intensity-dependent response of flicker ERGs in Rpe65+/+, Rpe65−/−, Rpe65−/− treated with 9-cis-retinal, and Rpe65−/− Rgr−/− mice. The flicker recordings were obtained with a range of intensities of 0.00040-41 cd·s/m² at a fixed frequency (10 Hz). Left panel, Rpe65+/+ mice; right panel, Rpe65−/− with or without treatment (open and closed circles, respectively) and Rpe65−/− Rgr−/− mice without treatment (closed triangles).

Figure 1A:
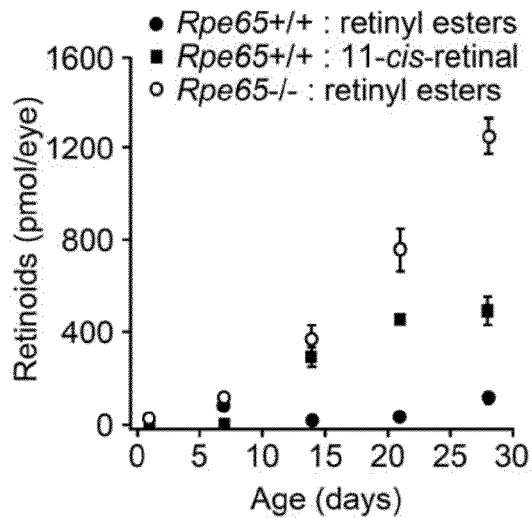
FIGS. 1A-1D. Changes in retinoid levels and interface between RPE and ROS in Rpe65−/− mice gavaged with 9-cis-retinal.

$$R/R_{max} = 1 - \exp^{ln2 \cdot i/Io} \quad \text{(Eq. 1)}$$

where R is the peak amplitude of the response, Rmax is the amplitude of the maximum response, and i is the flash strength in photons/µm². The solid lines are the exponential saturation function fitted to data with I0 (equivalent 500 nm photons/µm²): 25 (Rpe65+/+), 164 (2.5), 1995 (1.25), 3929 (0.25), and 3714 (0 mg of 9-cis-retinal). Inset, the kinetics of responses adapted by similar amounts (approximately 4-fold) by steady background illumination (336 equivalent 500-nm photons/µm²/s, black traces) in a Rpe65+/+ rod and by dark light (free opsin) in rod from Rpe65−/− mouse treated with 1.25 mg of 9-cis-retinal. Each trace is from a single rod and is the mean of 10-flashes either 6.25 (wild-type) or 910 (Rpe65−/− 1.25 mg of 9-cis-retinal (500 nm photon/µm²/flash).

FIGS. 4A-4C. Photosensitivity of 11-cis-7-ring-retinal isomers and substrate specificity of eye-specific RDHs. FIG. 4A, light sensitivity of 11-cis-7-ring-retinals and 11-cis-7-ring-hodopsin. The bleaching studies were carried out as described under "Methods and Materials" (Example 2 (infra)). The conditions for oxime formation from each isomer are described below for FIG. 4C. Activities of 11-cis-RDH (detergent-purified human recombinant 11-cis-RDH-His6) and all-trans-RDI (prRDH expressed in Sf9 cells) were determined by monitoring the production of the corresponding [15-$^3$H]retinol analog from the reduction of the 11-cis-ring-retinal isomer and pro-S-[4-$^3$]NADH (for 11-cis-RDH) or pro-S-[4-$^3$H]NADPH (for prRDH) (31) as described under "Methods and Materials" (Example 2 (infra)). The product was analyzed by normal phase HPLC, collected, and quantified by scintillation counting. FIG. 4B, the purification of 11-cis-ring-rhodopsin isomers was monitored by UV spectroscopy in each step. Trace a, the 71,700×g supernatant of 11-cis-ring-rhodopsin isomer 3 (solubilized by 10 mM n-dodecyl-β-D-maltoside); trace b, the flow-through fraction after the supernatant passed through a concanavalin A-Sepharose 4B column (see "Methods and Materials", Example 2 (infra)); trace c, the fraction after extensive wash of the concanavalin A-Sepharose 4B column; trace d, the purified 11-cis-7-ring-rhodopsin isomer 3; and trace e, the photobleached 11-cis-7-ring-rhodopsin isomer 3. FIG. 4C, normal phase HPLC analysis of oxime derivatives of 11-cis-7-ring-retinal isomers 1-4 in solution (HPLC traces i-viii, 1' and 1": 11-cis-7-ring-retinal isomer 1 oximes, syn and anti, respectively; 2' and 2": 11-7-cis-ring-retinal isomer 2 oximes, syn and anti, respectively; 3' and 3": 11-cis-7-ring-retinal isomer 3 oxime, syn and anti, respectively; and 4' and 4": 11-cis-7-ring-retinal isomer 4 oximes, syn and anti, respectively) and in rhodopsin 3 (ix and x) without (i, iii, v, vii, and ix) or with (ii, iv, vi, viii, and x) photobleaching. The 11-cis-7-ring-rhodopsin was solubilized with n-dodecyl-β-D-maltoside and purified over a concanavalin A-Sepharose 4B column. The purified fraction was subjected to photobleaching, and the chromophore(s) was derivatized with hydroxylamine and analyzed by HPLC as described under "Methods and Materials" (Example 2 (infra)). As controls, isomers 1-4 were also derivatized in the same elution buffer with or without photobleaching. *, contains minor amounts of compound 2 because of the unresolved peaks between compounds 2 and 3; mAU, milliabsorption units.

Figure 5:
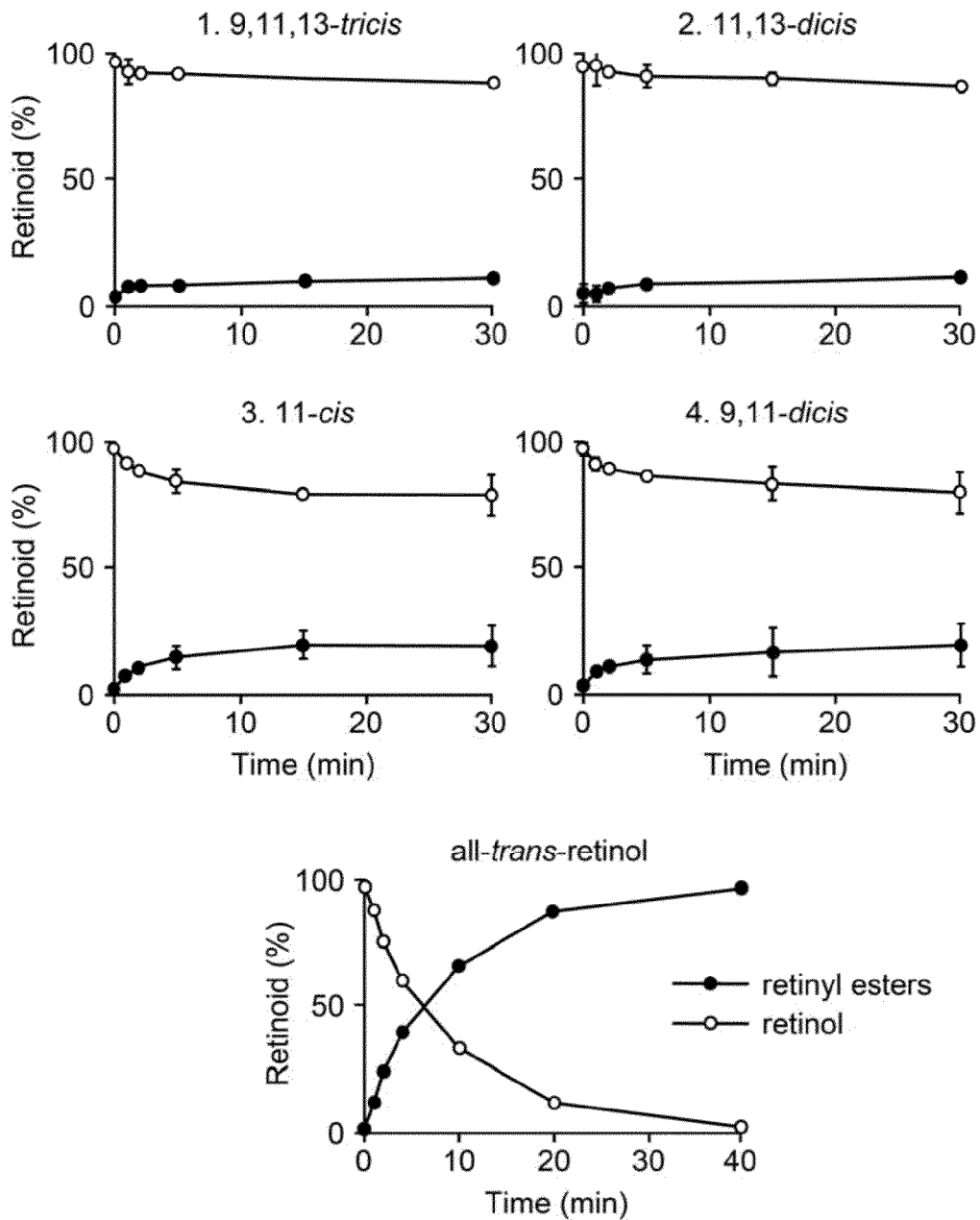

FIG. 5. LRAT activity toward different retinoids. Time course of LRAT activity with four 11-cis-ring-7-ring-retinol isomers, an average of two independent studies. Below is LRAT activity with all-trans-retinol, the native substrate for LRAT. Assays were performed as described under "Methods and Materials" (Example 2 (infra)).

Figure 6A:
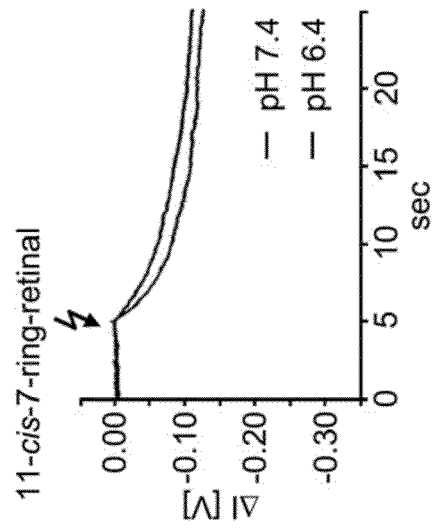
Figure 6B:
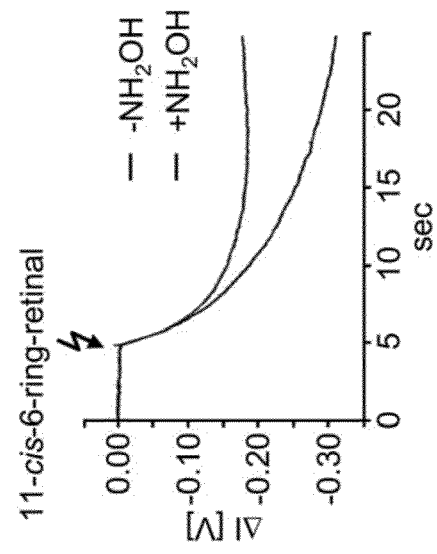
Figure 6C:
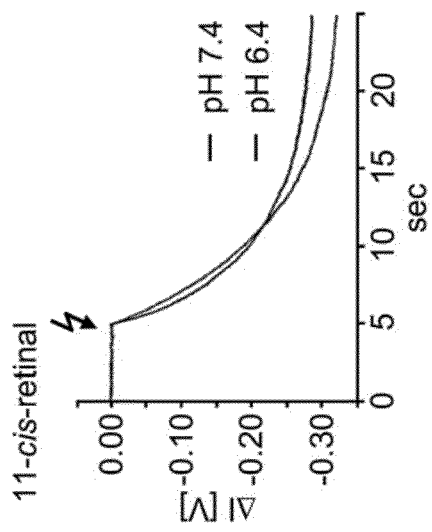
Figure 6D:
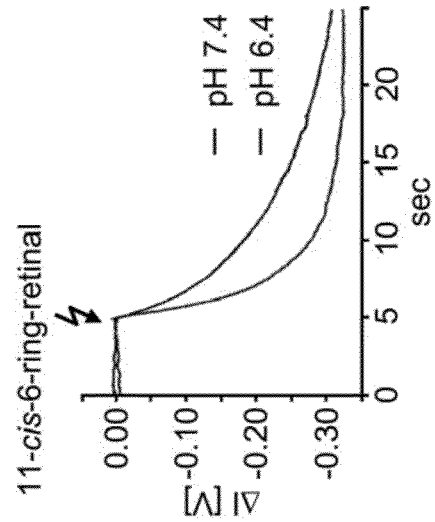

FIGS. 6A-6D. Dissociation of Gt in the presence of GTP as measured using light-scattering methods. FIG. 6A, the dissociation signal of the native sample at pH 7.4 and 6.4 evoked by a dim flash (Rh*/Rh=2.4×10$^{-4}$). These data show that according to the well known pH/rate profile at pH 7.4, a higher activity of receptor is observed compared with pH 6.4. FIGS. 6B and 6C, the dissociation signal of the photoproduct of Rh regenerated with the 11-cis-7-ring (isomer 1) (B) or 11-cis-6-ring (C) analogs at pH 6.4 and 7.4, respectively, evoked by a bright flash (1350-fold intensity as compared with A). FIG. 6D, sensitivity of 11-cis-6-ring-Rh to NH$_2$OH (2.5 mM) at pH 7.4.

DETAILED DESCRIPTION OF THE INVENTION

The present invention provides methods of restoring or stabilizing photoreceptor function in a vertebrate visual system. Synthetic retinoids can be administered to restore or stabilize photoreceptor function, and/or to ameliorate the effects of a deficiency in retinoid levels. Photoreceptor function can be restored or stabilized, for example, by providing a synthetic retinoid act as an 11-cis-retinoid replacement and/or an opsin agonist. The synthetic retinoid also can ameliorate the effects of a retinoid deficiency on a vertebrate visual system. A synthetic retinoid can be administered prophylactically or therapeutically to a vertebrate. Suitable vertebrates include, for example, human and non-human vertebrates. Suitable non-human vertebrates include, for example, mammals, such as dogs, cats, horses and other domesticated animals.

The synthetic retinoids are retinals derived from 11-cis-retinal or 9-cis-retinal, or are 9-cis-retinal. In certain embodiments, the "synthetic retinoid" is a "synthetic cis retinoid." In other embodiments, the synthetic retinoid is a derivative of 11-cis-retinal or 9-cis-retinal, with the proviso that the synthetic retinoid is not 9-cis-retinal. In yet other embodiments, the synthetic retinoid is not vitamin A. In some embodiments, a synthetic retinoid can, for example, be a retinoid replacement, supplementing the levels of endogenous retinoid. In additional embodiments, a synthetic retinoid can bind to opsin, and function as an opsin agonist. As used herein, the term "agonist" refers to a synthetic retinoid that binds to opsin and facilitates the ability of an opsin/synthetic retinoid complex to respond to light. As an opsin agonist, a synthetic retinoid can spare the requirement for endogenous retinoid. A synthetic retinoid also can restore function (e.g., photoreception) to opsin by binding to the opsin and forming a functional opsin/synthetic retinoid complex, whereby the opsin/synthetic retinoid complex can respond to photons when part of a rod or cone membrane.

Synthetic retinoids include 11-cis-retinal derivatives or 9-cis-retinal derivatives such as, for example, the following: acyclic retinals; retinals with modified polyene chain length, such as trienoic or tetraenoic retinals; retinals with substituted polyene chains, such as alkyl, halogen or heteratom-substituted polyene chains: retinals with modified polyene chains, such as trans- or cis-locked polyene chains, or with, for example, allene or alkyne modifications; and retinals with ring modifications, such as heterocyclic, heteroaromatic or substituted cycloalkane or cycloalkene rings.

In certain embodiments, the synthetic retinoid can be a retinal of the following formula I:

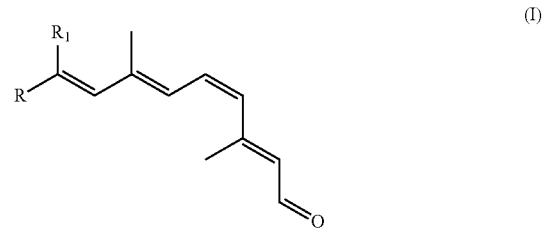

R and R1 can be independently selected from linear, iso-, sec-, tert- and other branched alkyl groups as well as substituted alkyl groups, substituted branched alkyl, hydroxyl, hydroalkyl, amine, amide, or the like. R and R1 can independently be lower alkyl, which means straight or branched alkyl with 1-6 carbon atom(s) such as methyl, ethyl, propyl, isopropyl, butyl, isobutyl, tert-butyl, pentyl, hexyl, or the like. Suitable substituted alkyls and substituted branch alkyls include, for example, alkyls, branched alkyls and cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

In certain additional embodiments, R or R1 can be a cycloalkyl such as, for example, hexane, cyclohexene, benzene as well as substituted cyclo-alkyl. Suitable substituted cyclo alkyl include, for example, cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

The synthetic retinoid also can be a derivative of an 11-cis-retinal or 9-cis-retinal that has a modified polyene chain length of the following formula II:

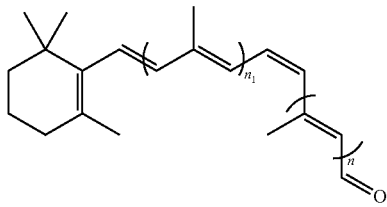

(II)

The polyene chain length can be extended by 1, 2, or 3 alkyl, alkene or alkylene groups. According to formula (II), each n and $n_1$ can be independently selected from 1, 2, or 3 alkyl, alkene or alkylene groups, with the proviso that the sum of the n and $n_1$ is at least 1.

The synthetic retinoid also can be a derivative of an 11-cis-retinal or 9-cis-retinal that has a substituted polyene chain of the following formula III:

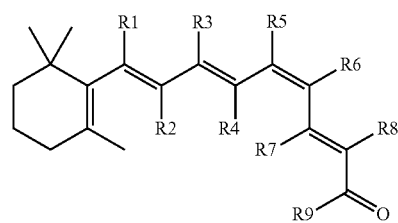

(III)

Each of R1 to R9 can be independently selected from hydrogen, alkyl, branched alkyl, cyclo-alkyl, halogen, a heteratom, or the like. Suitable alkyls include, for example, methyl, ethyl, propyl, substituted alkyl (e.g., alkyl with hydroxyl, hydroalkyl, amine, amide) or the like. Suitable branched alkyl can be, for example, isopropyl, isobutyl, substituted branched alkyl, or the like. Suitable cyclo-alkyls can include, for example, cyclohexane, cycloheptane, and other cyclic alkanes as well as substituted cyclic alkanes such as substituted cyclohexane or substituted cycloheptane. Suitable halogens include, for example, bromine, chlorine, fluorine, or the like. Suitable heteroatoms include, for example, sulfur, silicon, and fluoro- or bromo-substitutions. Suitable substituted alkyls, substituted branch alkyls and substituted cyclo-alkyls include, for example, alkyls, branched alkyls and cyclo-alkyls substituted with oxygen, hydroxyl, nitrogen, amide, amine, halogen, heteroatom or other groups. In exemplary embodiments, the synthetic retinoid is 9-ethyl-11-cis-retinal, 7-methyl-1-cis-retinal, 13-desmethyl-11-cis-retinal, 11-cis-10-F-retinal, 11-cis-10-Cl-retinal, 11-cis-10-methyl-retinal, 11-cis-10-ethyl-retinal, 9-cis-10-F-retinal, 9-cis-10-Cl-retinal, 9-cis-10-methyl-retinal, 9-cis-10-ethyl-retinal, 11-cis-12-F-retinal, 11-cis-12-Cl-retinal, 11-cis-12-methyl-retinal, 11-cis-10-ethyl-retinal, 9-cis-12-F-retinal, 9-cis-12-Cl-retinal, 9-cis-12-methyl-retinal 11-cis-14-F-retinal, 11-cis-14-methyl-retinal, 11-cis-14-ethyl-retinal, 9-cis-14-F-retinal, 9-cis-14-methyl-retinal, 9-cis-14-ethyl-retinal, or the like.

The synthetic retinoid further can be derivative of an 11-cis-retinal or 9-cis-retinal that has a modified ring structure. Suitable examples include, for example, derivatives containing ring modifications, aromatic analogs and heteroaromatic analogs of the following formulae IV, V and VI, respectively:

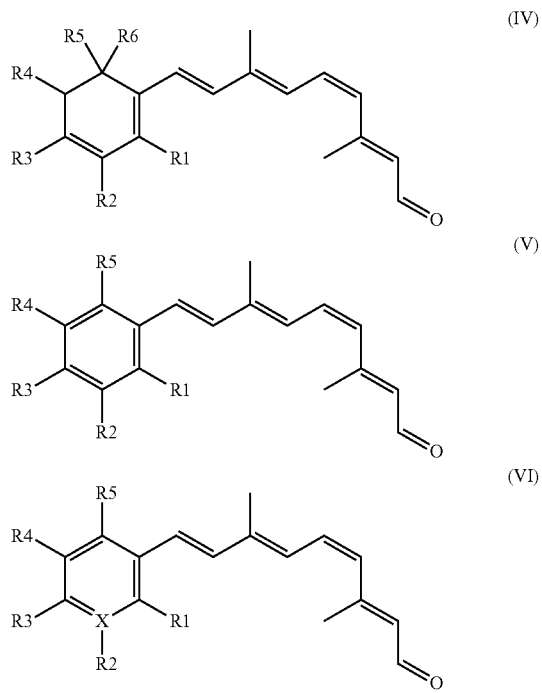

Each of R1 to R5 or R6, as applicable, can be independently selected from hydrogen, alkyl, substituted alkyl, hydroxyl, hydroalkyl, amine, amide, halogen, a heteroatom, or the like. Suitable alkyls include, for example, methyl, ethyl, propyl, isopropyl, butyl, isobutyl or the like. Suitable halogens include, for example, bromine, chlorine, fluorine, or the like. Suitable heteroatoms include, for example, sulfur, silicon, or nitrogen. In formulae VI, X can be, for example, sulfur, silicon, nitrogen, fluoro- or bromo-substitutions.

The synthetic retinoid can further be a derivative of an 11-cis-retinal or 9-cis-retinal that has a modified polyene chain. Suitable derivatives include, for example, those with a trans/cis locked configuration, 6s-locked analogs, as well as modified allene, alkene, alkyne or alkylene groups in the polyene chain. In one example, the derivative is an 11-cis-locked analog of the following formula VII:

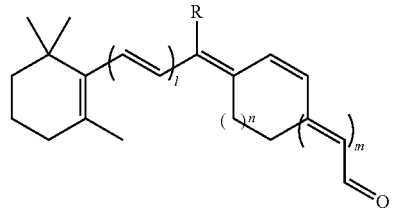

(VII)

R can be, for example, hydrogen, methyl or other lower alkane or branch alkane, n can be 0 to 4, m plus 1 equals 1, 2 or 3.

In a specific embodiment, the synthetic retinoid is a 11-cis-locked analog of the following formula VIII:

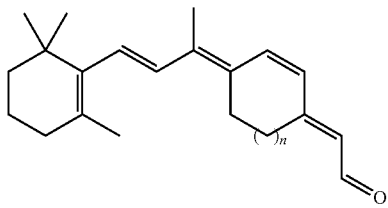

(VIII)

n can be 1 to 4.

In certain exemplary embodiments, the synthetic retinoid is 9,11,13-tri-cis-7-ring retinal, 11,13-di-cis-7-ring retinal, 11-cis-7-ring retinal or 9,11-di-cis-7-ring retinal.

In another example, the synthetic retinoid is a 6s-locked analog of formula IX. R1 and R2 can be independently selected from hydrogen, methyl and other lower alkyl and substituted lower alkyl. R3 can be independently selected from an alkene group at either of the indicated positions.

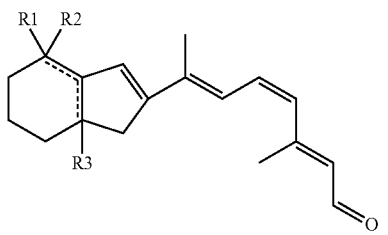

(IX)

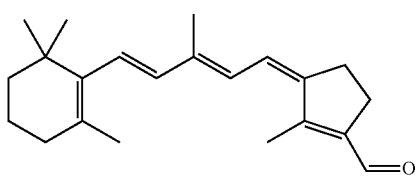

(X)

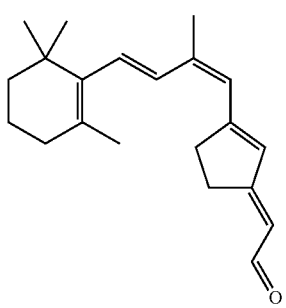

(XI)

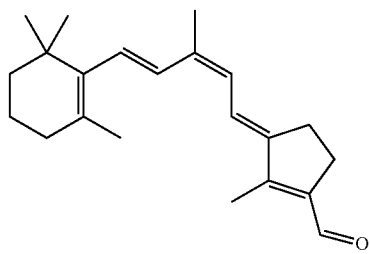

(XII)

In other embodiments, the synthetic retinoid can be a 9-cis-ring-fused derivative, such as, for example, those shown in formulae X-XII.

In yet another embodiment, the synthetic retinoid is of the following formula XIII.

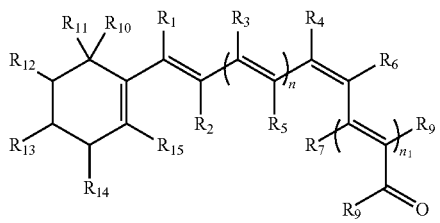

Each of R1 to R15 can be independently selected from hydrogen, alkyl, branched alkyl, halogen, hydroxyl, hydroalkyl, amine, amide, a heteratom, or the like. Suitable alkyls include, for example, methyl, ethyl, propyl, substituted alkyl (e.g., alkyl with hydroxyl, hydroalkyl, amine, amide), or the like. Suitable branched alkyl can be, for example, isopropyl, isobutyl, substituted branched alkyl, or the like. Suitable halogens include, for example, bromine, chlorine, fluorine, or the like. Suitable heteroatoms include, for example, sulfur, silicon, and fluoro- or bromo-substitutions. Suitable substituted alkyls and substituted branch alkyls include, for example, alkyls and branched alkyls substituted with oxygen, hydroxyl, nitrogen, amide, amine, halogen, heteroatom or other groups. Each of n and $n_1$ can be independently selected from 1, 2, or 3 alkyl, alkene or alkylene groups, with the proviso that the sum of the n and $n_1$ is at least 1. In addition, R11-R12 and/or R13-R14 can comprise an alkene group in the cyclic carbon ring. In certain embodiments, R5 and R7 together can form a cyclo-alkyl, such as a five, six, seven or eight member cyclo-alkyl or substituted cyclo-alkyl, such as, for example, those shown in formulae VII, VIII, X, XI and XII.

In additional embodiments, the synthetic retinoid also can be 9-cis-retinal. Alternatively, 11-cis-retinal can be used.

Methods of making synthetic retinoids are disclosed in, for example, the following references: *Anal. Biochem.* 272:232-42 (1999); *Angew. Chem.* 36:2089-93 (1997); *Biochemistry* 14:3933-41 (1975); *Biochemistry* 21:384-93 (1982); *Biochemistry* 28:2732-39 (1989); *Biochemistry* 33:408-16 (1994); *Biochemistry.* 35:6257-62 (1996); *Bioorganic Chemistry* 27:372-82 (1999); *Biophys. Chem.* 56:31-39 (1995); *Biophys. J.* 56:1259-65 (1989); *Biophys. J.* 83:3460-69 (2002); *Chemistry* 7:4198-204 (2001); *Chemistry* (Europe) 5:1172-75 (1999); *FEBS* 158:1 (1983); *J. American Chem. Soc.* 104:3214-16 (1982); *J. Am. Chem. Soc.* 108:6077-78 (1986); *J. Am. Chem. Soc.* 109:6163 (1987); *J. Am. Chem. Soc.* 112:7779-82 (1990); *J. Am. Chem. Soc.* 119:5758-59

(1997); *J. Am. Chem. Soc.* 121:5803-04 (1999); *J American Chem. Soc.* 123:10024-29 (2001); *J. American Chem. Soc.* 124:7294-302 (2002); *J. Biol. Chem.* 276:26148-53 (2001); *J. Biol. Chem.* 277:42315-24 (2004); *J. Chem. Soc.—Perkin T.* 1:1773-77 (1997); *J. Chem. Soc.—Perkin T.* 1:2430-39 (2001); *J. Org. Chem.* 49:649-52 (1984) *J. Org. Chem.* 58:3533-37 (1993); *J. Physical Chemistry B* 102:2787-806 (1998); *Lipids* 8:558-65; *Photochem. Photobiol.* 13:259-83 (1986); *Photochem. Photobiol.* 44:803-07 (1986); *Photochem. Photobiol.* 54:969-76 (1991); *Photochem. Photobiol.* 60:64-68 (15994): *Photochem. Photobiol.* 65:1047-55 (1991): *Photochem. Photobiol.* 70:111-15 (2002); *Photochem. Photobiol.* 76:606-615 (2002); *Proc. Natl. Acad. Sci. USA* 88:9412-16 (1991); *Proc. Natl. Acad. Sci. USA* 90:4072-76 (1993); *Proc. Natl Acad. Sci. USA* 94:13442-47 (1997): and *Proc. R. Soc. Lond. Series B. Biol. Sci.* 233(1270): 55-76 1988) (the disclosures of which are incorporated by reference herein).

For an opsin protein, synthetic retinoids can be identified, for example, by an expression system expressing the opsin protein. Suitable animal models include, for example, RPE65−/− mice (see infra). Suitable non-human animal models further include rat, mouse, primate systems. Such animal models can be prepared, for example, by promoting homologous recombination between a nucleic acid encoding an opsin in its chromosome and an exogenous nucleic acid encoding a mutant opsin. In one aspect, homologous recombination is carried out by transforming embryo-derived stem (ES) cells with a vector containing an opsin gene, such that homologous recombination occurs, followed by injecting the ES cells into a blastocyst, and implanting the blastocyst into a foster mother, followed by the birth of the chimeric animal (see, e.g., Capecchi, *Science* 244:1288-92 (1989)). The chimeric animal can be bred to produce additional transgenic animals.

Suitable expression systems can include, for example, in vitro or in vivo systems. Suitable in vitro systems include for example, coupled transcription-translation systems. Suitable in vivo systems include, for example, cells expressing an opsin protein. For example, cells of a vertebrate visual system can be adapted for culture in vitro, or recombinant cell lines expressing an opsin protein can be used. The cell lines are typically stable cell lines expressing the opsin protein. Synthetic retinoid can be added to the cell culture media, and the cells cultured for a suitable period of time to allow the production of opsin/rhodopsin. Opsin and/or rhodopsin can be isolated (e.g., by immunoaffinity). Isolated protein samples are examined to determine the amount of pigment formed, and absorbance maxima. Methods of introducing nucleic acids into vertebrate cells are disclosed in, for example, Sambrook et al., *Molecular Cloning: A Laboratory Manual*, Cold Spring Harbor Laboratory Press (Cold Spring Harbor, N.Y., 2001).

Recombinant cell lines expressing opsin protein can be prepared by, for example, introducing an expression construct encoding an opsin protein into a suitable cell line. The expression construct typically includes a promoter operably linked to a nucleic acid encoding an opsin protein, and optionally a termination signal(s). Nucleic acids encoding opsin can be obtained, for example, by using information from a database (e.g., a genomic or cDNA library), by polymerase chain reaction, or the like. For example opsin encoding nucleic acids can be obtained by hybridization. (See generally Sambrook et al. (supra).) In a specific embodiment, an opsin encoding nucleic acid can be obtained by hybridization under conditions of low, medium or high stringency.

In certain embodiments, opsin encoding nucleic acids can be obtained under conditions of high stringency hybridization. By way of example, and not limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters is done at 65° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art. (See generally Sambrook et al. (supra).)

The expression construct can optionally include one or more origins of replication and/or selectable marker(s) (e.g., an antibiotic resistance gene). Suitable selectable markers include, for example, those conferring resistance to ampicillin, tetracycline, neomycin, G418, and the like. Suitable cell lines include, for example, HEK293 cells, T-Rex™-293 cells, CHO cells and other cells or cell lines.

The UV-visible spectra of rhodopsin (comprising opsin and a synthetic retinoid) can be monitored to determine whether the synthetic retinoid has formed a Schiff's base with the opsin protein. For example, acid-denatured, purified protein can be analyzed to determine whether an absorbance maxima of approximately 440 nm is present, providing evidence that the synthetic retinoid forms a Schiff's base with the opsin protein. In additional embodiments, hydroxylamine treatment can be used to confirm the Schiff's base is sequestered from the external environment (infra).

Suitable synthetic retinoids also can be selected by molecular modeling of rhodopsin. The coordinates for rhodopsin crystal structure are available from the Protein Data Bank (1HZX) (Teller et al., *Biochemistry* 40:7761-72 (2001)). In certain embodiments, the effects of amino acid substitutions on the structure of rhodopsin, and on the contacts between opsin and 11-cis-retinal, or a synthetic retinoid, can be determined by molecular modeling.

In an exemplary embodiment, the coordinates for the rhodopsin crystal structure from the Protein Data Bank (1HZX) (Teller et al., *Biochemistry* 40:7761-72 (2001)) are used to generate a computer model. The addition of hydrogen atoms and optimization can be done, for example, using Insight II (InsightII release 2000, Accelrys, Inc., San Diego, Calif.). Crystallographic water can be removed, and water molecules introduced based on the accessible space in the extracellular region. Typically, no minimization is performed before water is added. A water layer (e.g., 5 Å thick) can be used to coat the extracellular part of rhodopsin as well as residues in contact with polar phospholipids heads. All of the water molecules can be allowed to move freely, as is the extracellular half of rhodopsin, with retinal. If no water cap is put on the cytoplasmic part of rhodopsin, this part of the molecule can be frozen to prevent degradation of the model.

In certain embodiments, a water cap is put on the extracellular part of rhodopsin (together with that part buried in membrane in contact with polar heads of phospholipids). Water and the extracellular part of rhodopsin can be allowed to move and the movement modeled at any suitable frequency. For example, the movement of the modeled rhodopsin can be modeling at 100 ps simulations.

Synthetic retinoids can be contacted with an opsin protein under conditions suitable and for a period of time sufficient for the formation of an opsin protein/synthetic retinoid complex. The stability of the opsin/synthetic retinoid complex can be determined by methods described herein or as known to the skilled artisan. The opsin in the opsin/synthetic retinoid complex is stabilized when it exhibits increased stability (e.g., increased half-life when bound to the synthetic retinoid as compared with free opsin (i.e., not bound to retinoid), is less sensitive to hydroxylamine, exhibits less accumulation in aggresomes, or the like).

The synthetic retinoid can be contacted with the opsin protein in vitro or in vivo. For example, the opsin protein can be synthesized in an in vitro translation system (e.g., a wheat germ or reticulocyte lysate expression system) and the synthetic retinoid added to the expression system. In additional embodiments, the opsin protein can be contacted with the opsin protein ex vivo, and then the complex can be administered to a vertebrate eye.

A synthetic retinoid can be administered to vertebrate eyes having a retinoid deficiency (e.g., a deficiency of 11-cis-retinal), an excess of free opsin, an excess of retinoid waste products (see infra) or intermediates in the recycling of all-trans-retinal, or the like. The vertebrate eye typically comprises a wild-type opsin protein. Methods of determining endogenous retinoid levels in a vertebrate eye, and a deficiency of such retinoids, are disclosed in, for example, U.S. Provisional Patent Application No. 60/538,051 (filed Feb. 12, 2004) (the disclosure of which is incorporated by reference herein). Other methods of determining endogenous retinoid levels in a vertebrate eye, and a deficiency of such retinoids, include for example, analysis by high pressure liquid chromatography (HPLC) of retinoids in a sample from a subject. For example, retinoid levels or a deficiency in such levels can be determined from a blood sample from a subject.

In an exemplary embodiment, a blood sample can be obtained from a subject and retinoid types and levels in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. A deficiency in retinoids can be determined, for example, by comparison of the profile of retinoids in the sample with a sample from a normal subject.

As used herein, absent, deficient or depleted levels of endogenous retinoid, such as 11-cis-retinal, refer to levels of endogenous retinoid lower than those found in a healthy eye of a vertebrate of the same species. A synthetic retinoid can spare the requirement for endogenous retinoid.

As used herein, "prophylactic" and "prophylactically" refer to the administration of a synthetic retinoid to prevent deterioration or further deterioration of the vertebrate visual system, as compared with a comparable vertebrate visual system not receiving the synthetic retinoid. The term "restore" refers to a long-term (e.g., as measured in weeks or months) improvement in photoreceptor function in a vertebrate visual system, as compared with a comparable vertebrate visual system not receiving the synthetic retinoid. The term "stabilize" refers to minimization of additional degradation in a vertebrate visual system, as compared with a comparable vertebrate visual system not receiving the synthetic retinoid.

In one aspect, the vertebrate eye is characterized as having Leber Congenital Amaurosis ("LCA"). This disease is a very rare childhood condition that effects children from birth or shortly there after. It affects both rods and cones in the eye. For example, certain mutations in the genes encoding RP65 and LRAT proteins are involved in LCA. Mutations in both genes result in a person's inability to make 11-cis-retinal in adequate quantities. Thus, 11-cis-retinal is either absent or present in reduced quantities. In RP65-defective individuals, retinyl esters build up in the RPE. LRAT-defective individuals are unable to make esters and subsequently secrete any excess retinoids. For LCA, a synthetic cis-retinoid can be used to replace the absent or depleted 11-cis-retinal.

In another aspect, the vertebrate eye is characterized as having Retinitis Punctata Albesciens. This disease is a form of Retinitis Pigmentosa that exhibits a shortage of 11-cis-retinal in the rods. A synthetic cis-retinoid can be used to replace the absent or depleted 11-cis retinal.

In another aspect, the vertebrate eye is characterized as having Congenital Stationary Night Blindness ("CSNB") or Fundus Albipunctatus. This group of diseases is manifested by night blindness, but there is not a progressive loss of vision as in the Retinitis Pigmentosa. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown recently that this is also a progressive disease, although with a much slower progression than Retinitis Pigmentosa. It is caused by a gene defect that leads to a delay in the cycling of 11-cis-retinal. Thus, synthetic retinoids can be administered to restore photoreceptor function by retinoid replacement.

In yet another aspect, the vertebrate eye is characterized as having age-related macular degeneration ("AMD"). In various embodiments. AMD can be wet or dry forms. In AMD, vision loss occurs when complications late in the disease either cause new blood vessels to grow under the retina or the retina atrophies. Without intending to be bound by any particular theory, excessive production of waste products from the photoreceptors may overload the RPE. This is due to a shortfall of 11-cis-retinal available to bind opsin. Free opsin is not a stable compound and can spontaneously cause firing of the biochemical reactions of the visual cascade without the addition of light.

Administration of a synthetic retinoid to the vertebrate eye can quench the deficiency of 11-cis-retinal and spontaneous misfiring of the opsin. In certain embodiments, administration of a synthetic retinoid can lessen the production of waste products and/or lessen drusen formation, and reduce or slow vision loss (e.g., choroidal neovascularization and/or chorioretinal atrophy).

In yet other aspects, a synthetic retinoid is administered to an aging subject. As used herein, an aging human subject is typically at least 45, or at least 50, or at least 60, or at least 65 years old. The subject has an aging eye, which is characterized as having a decrease in night vision and/or contrast sensitivity. Excess unbound opsin randomly excites the visual transduction system. This creates noise in the system and thus more light and more contrast are necessary to see well. Quenching these free opsin molecules with a synthetic retinoid will reduce spontaneous misfiring and increase the signal to noise ratio, thereby improving night vision and contrast sensitivity.

Synthetic retinoids can be administered to human or other non-human vertebrates. Synthetic retinoids can be delivered to the eye by any suitable means, including, for example, oral or local administration. Modes of local administration can include, for example, eye drops, intraocular injection or periocular injection. Periocular injection typically involves injection of the synthetic retinoid into the conjunctiva or to the tennon (the fibrous tissue overlying the eye). Intraocular injection typically involves injection of the synthetic retinoid into the vitreous. In certain embodiments, the administration is non-invasive, such as by eye drops or oral dosage form.

Synthetic retinoids can be formulated for administration using pharmaceutically acceptable vehicles as well as techniques routinely used in the art. A vehicle is selected according to the solubility of the synthetic retinoid. Suitable ophthalmological compositions include those that are administrable locally to the eye, such as by eye drops, injection or the like. In the case of eye drops, the formulation can also optionally include, for example, isotonizing agents such as sodium chloride, concentrated glycerin, and the like: buffering agents such as sodium phosphate, sodium acetate, and the like; surfactants such as polyoxyethylene sorbitan monooleate (also referred to as Polysorbate 80), polyoxyl stearate 40, polyoxyethylene hydrogenated castor oil, and the like; stabilization agents such as sodium citrate, sodium edentate, and the like: preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the synthetic retinoid can be provided in an injection grade saline solution, in the form of an injectable liposome solution, or the like. Intraocular and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pages 85-87 (1990).

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington "Pharmaceutical Sciences"*, 17 Ed., Gennaro (ed.). Mack Publishing Co., Easton, Pa. (1985).)

The doses of the synthetic retinoids can be suitably selected depending on the clinical status, condition and age of the subject, dosage form and the like. In the case of eye drops, a synthetic retinoid can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the synthetic retinoid, one to lour times per week. In other embodiments, about 1.0 to about 30 mg of synthetic retinoid can be administered one to three times per week.

Oral doses can typically range from about 1.0 to about 1000 mg, one to four times, or more, per day. An exemplary dosing range for oral administration is from about 10 to about 250 mg one to three times per day.

The following examples are provided merely as illustrative of various aspects of the invention and shall not be construed to limit the invention in any way.

EXAMPLES

Example 1

The visual process is initiated by the photoisomerization of 11-cis-retinal to all-trans-retinal. For sustained vision, the 11-cis-chromophore must be regenerated from all-trans-retinal. This requires RPE65, a dominant retinal pigment epithelium protein. Disruption of the RPE65 gene results in massive accumulation of all-trans-retinyl esters in the retinal pigment epithelium, lack of 11-cis-retinal and therefore rhodopsin, and ultimately blindness. It was previously reported that in Rpe65−/− mice, oral administration of 9-cis-retinal generated isorhodopsin (a rod photopigment) and restored light sensitivity to the electroretinogram (Van Hooser et al., *Proc. Natl. Acad. Sci. USA* 97:8623-28 (2000)). In this study, early intervention by 9-cis-retinal administration significantly attenuated retinal ester accumulation and supported rod retinal function for more than 6 months post-treatment. In single cell recordings, rod light sensitivity was shown to be a function of the amount of regenerated isorhodopsin: high doses restored rod responses with normal sensitivity and kinetics. Highly attenuated residual rod function was observed in untreated Rpe65−/− mice. This rod function is likely a consequence of low efficiency production of 11-cis-retinal by photo-conversion of all-trans-retinal in the retina as demonstrated by retinoid analysis. These studies show that pharmacological intervention produces long lasting preservation of visual function in dark-reared Rpe65−/− mice and will be a useful therapeutic strategy in recovering vision in humans diagnosed with Leber congenital amaurosis caused by mutations in the RPE65 gene, an inherited group of early onset blinding and retinal degenerations.

Introduction

Leber congenital amaurosis (LCA) is a group of conditions that cause blindness or severe visual impairment from birth. All show both rod and cone dysfunction, a negligible (not recordable) electroretinogram (ERG), and nystagmus. They result in early onset retinal dystrophy, which over time may be accompanied by pigmentary changes in the retina, hence "amaurosis." LCA is caused by defects in at least five different genes that disrupt a variety of different cellular functions.

In approximately 12% of all LCA cases the gene for a 65-kDa protein (RPE65) of retinal pigment epithelium cells (RPE) is disabled. RPE65 is heavily expressed in RPE cells, where it plays an essential role in the retinoid cycle. This is a set of tightly interconnected events that involve both photoreceptors and RPE cells. The photoisomerization of the visual pigment chromophore (11-cis-retinal) produces all-trans-retinal, which is reduced in the photoreceptor, transferred to the RPE, converted back to 11-cis-retinal, and then transferred back to the photoreceptor to regenerate the original visual pigment. The precise function of RPE65 in retinoid processing is unknown.

Genetically engineered mice in which the gene for Rpe65 has been eliminated (Rpe65−/−) exhibit changes in retinal morphology, function, and biochemistry that closely resemble the changes seen in human LCA patients. Both rod and cone function is severely disrupted, and the ERG is severely attenuated in Rpe65−/− mice. There is also a dramatic overaccumulation of all-trans-retinyl esters in the RPE cells in lipid-like droplets and degeneration of the retina. Thus, the Rpe65−/− mouse provides the opportunity to gain insight into the cellular and molecular origins and consequences of LCA as well as a means to test different therapeutic strategies.

This study describes the results of an in-depth study of the changes in biochemistry and function that occur in Rpe65−/− mice and show how the progression of the disease can be interrupted and the functional effects reversed by providing a supply of 9-cis-retinal. The goals were to: 1) examine the beneficial effects of 9-cis-retinal treatment on the progression of the disease and on photoreceptor function; 2) evaluate using single cell electrophysiology and ERG recording how 9-cis-retinal treatment affected rod function and light-driven signals in the retina; and 3) investigate the biochemical basis for the low level of residual vision that persists in both LCA patients and Rpe65−/− mice.

Administration of 9-cis-retinal to Rpe65−/− mice produces and maintains rod photopigment for more than 6 months in the dark. Early intervention with 9-cis-retinal restores normal rod physiology and significantly attenuates ester accumulation in the RPE, but only partially improves retinal function as measured by ERG. These studies demonstrate that pharmacological intervention produces long lasting preservation of visual function in dark-reared Rpe65−/− mice and is a useful therapy for restoring vision in LCA patients.

Materials and Methods

Animals: All of the animal studies employed procedures approved by the University of Washington Animal Care Committee and conformed with recommendations of the American Veterinary Medical Association Panel on Euthanasia. Animals were maintained in complete darkness, and all of the manipulations were performed under dim red light employing all Kodak No. 1 Safelight filter (transmittance, >560 nm). Typically, 2-3-month-old mice were used in all of the studies. RPE65-deficient mice were obtained from Dr. M. Redmond (NEI, National Institutes of Health) and genotyped as described previously (Redmond et al., *Nat. Genet.* 20:344-51 (1998); Redmond et al., *Methods Enzymol.* 316:70524 (2000)). Retinal G protein-coupled receptor-deficient mice were generated and genotyped as described previously (Chen et al., *Nat. Genet.* 28:256-60 (2001)). Double knockout Rpe65−/− Rgr−/− were generated by cross-breeding single Rpe65−/− and Rgr−/− mice to genetic homogeneity.

Analyses of Retinoids and Visual Pigments:

All of the procedures were performed under dim red light as described previously (Van Hooser et al., *Proc. Natl. Acad. Sci. USA* 97:8623-28 (2000); Jang et al., *J. Biol. Chem.* 276:32456-65 (2001); Palczewski et al., *Biochemistry* 38:12012-19 (1999)). In addition to previously described methods, retinoid analysis was performed on an HP 1100 series high pressure liquid chromatograph (HPLC) equipped with a diode array detector and HP Chemstation A.07.01 software, allowing identification of retinoid isomers according to their specific retention time and absorption maxima. A normal phase column (Beckman Ultrasphere Si 5µ, 4.6×250 mm) and an isocratic solvent system of 0.5% ethyl acetate in hexane (v/v) for 15 minutes followed by 4% ethyl acetate in hexane for 60 minutes at a flow rate of 1.4 ml/minute at 20° C. (total 75 min) with detection at 325 nm allowed the separation of 11-cis-, 13-cis-, and all-trans-retinyl esters. In addition, all of the study procedures related to the analysis of dissected mouse eyes, derivatization, and separation of retinoids have been described previously in detail (Van Hooser et al., *Proc. Natl. Acad. Sci. USA* 97:8623-28 (2000)). Rhodopsin and iso-rhodopsin measurements were performed as described previously (Palczewski et al., *Biochemistry* 38:12012-19 (1999)). Typically, two mouse eyes were used per assay, and the assays were repeated three to six times. The data are presented with S.E.M.

Light and Electron Microscopy:

Eye cups were prepared by removing the anterior segment and vitreous. The eyes were collected on ice at PND 1-28 on a weekly basis. "Thin" sections (1.0 µm) were stained with Richardson's blue solution (1%) and subjected to light microscopy. "Ultrathin" sections (0.05 µm) were stained with uranyl acetate/lead citrate and subjected to electron microscopy.

Preparation of Mouse RPE Microsomes:

Fresh mouse eyes were enucleated immediately after cervical dislocation or $CO_2$ asphyxiation. The anterior segment, vitreous, and retina were carefully removed under a micro-dissecting scope. Typically, 30-40 eyes were dissected for each preparation. RPE cells were separated by placing 12 dissected eyecups in 400 µl of 10 mM MOPS, pH 7.0, containing 1 µM leupeptin and 1 mM dithiothreitol and vigorously shaken for 20 minutes. The eyecups were then gently brushed with a fine brush to further dislodge the RPE cells. The cell suspension was removed, another aliquot of 400 µl of MOPS buffer was added, and the eyecups were shaken again for 20 minutes. The cell suspensions were combined and subjected to glass-glass homogenization. The homogenate was centrifuged at 10,000×g for 10 min, and then the supernatant was centrifuged at 275,000×g for 1 hour. The pellet was then reconstituted in 200 µl of the MOPS buffer and resubjected to glass-glass homogenization. The total protein concentration (typically 0.5-1 mg/ml) was determined by the Bradford method. (See. e.g., Bradford. *Anal. Biochem.* 72:248-54 (1976).)

Isomerization of All-Trans-Retinol to 11-Cis-Retinol Using Mouse RPE Microsomes:

The assay used for determining isomerization to 11-cis-retinol was reported previously (McBee et al. *Biochemistry* 39:11370-70 (2000)). Briefly, 20 µl of bovine serum albumin (final concentration, 1%), 125 µl of 50 mM 1,3-bis[tris(hydroxymethyl)-methylamino]propane, pH 7.5, 10 µl of ATP (1 mM final concentration), 25 µM apo-recombinant CRALBP, 40 µl of RPE microsomes (typically 25-50 µg of total protein), and 0.5 µl of 4 mM all-trans-retinol in dimethylformamide. The reactions were incubated for 2 hours at 37° C. The reaction was quenched using 300 µl of MeOH, and the retinoids were extracted with 200 µl of hexane. The mixture was shaken vigorously for 2 minutes and then centrifuged at 14,000 rpm for 4 minutes for phase separation. The upper organic layer was removed, and a 100 µl aliquot was separated and analyzed using an HP 1100 HPLC (Beckman Ultrasphere Si, 4.6 mm×250 mm, 1.4 ml/minute flow rate using 10% ethyl acetate in hexane) equipped with HP Chemstation software (version A.07.01).

Preparation of Pro-S-[4-$^3$H]NADH and Pro-S-[4-$^3$H] NADPH:

Syntheses of pro-S-[4-$^3$H]NADH and pro-S-[4-$^3$H] NADPH were carried out with L-glutamic dehydrogenase, NAD(P), and L-[2,3-$^3$H]glutamic acid (PerkinElmer Life Sciences), as described previously (Jang et al., *J. Biol. Chem.* 276:32456-65 (2001); Jang et al. *J. Biol. Chem.* 275:28128-38 (2000)).

RDH Assays:

The assays were carried out by monitoring the production of [15-$^3$H]retinol (reduction of retinal) using 11-cis-retinal and pro-S-[4-$^3$H]NAD(P)H as dinucleotide substrates in the presence or absence of NADH (see, e.g., McBee et al., *Prog. Retin. Eye Res.* 20:469-529 (2001)).

Oral Gavage:

Oral gavage was carried out as described previously (Van Hooser et al., *Proc. Natl. Acad. Sci. USA* 97:8623-28 (2000)).

Intravenous Administration of Retinoids:

The chemicals were purchased from Sigma/Aldrich unless otherwise specified. Solution A contained 10 mg of 9-cis-retinal, 75 mg of Cremophor EL, 1 mg of α-tocopherol, and 0.6 mg of benzoic acid suspended in 1 ml of lactated Ringer's solution (Baxter). The mixture was vortexed for 10 minutes and centrifuged for 10 minutes at 20,000×g, and the concentration of 9-cis-retinal (7.7 mM) was determined spectrophotometrically. Solution B contained 13 mg of 9-cis-retinal, 50 mg of Cremophor EL, 10 mg of dipalmitoylphosphatidyl choline, and 40 mg of 2-hydroxypropyl-β-cyclodextrin suspended in 1 ml of lactated Ringer's solution (Baxter). The mixture was vortexed for 10 minutes and centrifuged for 10 minutes at 20,000×g, and the concentration of 9-cis-retinal (10 mM) was determined spectrophotometrically. Solutions A and B (typically, 100 μl) were delivered to the mouse lateral tail vein employing a 1-ml syringe equipped with a 27-gauge needle and a restraint tube.

Single Cell Recordings:

Mice were dark-reared from birth and sacrificed via cervical dislocation, and the eyes were removed. The retina was isolated and stored on ice for up to 12 hours in HEPES-buffered Ames' solution (10 mM HEPES, pH adjusted to 7.4 with NaOH). Isolated rods were obtained by shredding a small piece of retina (roughly 1 mm$^2$) with fine needles in a 160-μl drop of solution. The drop was then injected into a recording chamber mounted on the stage of an inverted microscope (Nikon Eclipse) equipped with an infrared video viewing system and continuously superfused at 2-3 ml/minute with bicarbonate-buffered Ames' solution warmed to 37° C. (pH 7.4 when equilibrated with 5% CO2, 95% $O_2$). The entire dissection was carried out under infrared illumination using a dissecting microscope equipped with infrared-visible image converters.

An isolated rod was drawn by suction into a heat-polished, silanized borosilicate electrode with an opening 1.2-1.5 μm in diameter. The electrode was filled with HEPES-buffered Ames' solution. The electrical connections to the bath and suction electrode were made by NaCl-filled agar bridges that contacted calomel half-cells. Bath voltage was held at ground by an active clamp circuit (Baylor et al. *J. Physiol.* 354:203-23 (1984)). Membrane current collected by the suction electrode was amplified by an Axopatch 200A patch clamp amplifier (Axon Instruments, Foster City, Calif.), filtered at 30 Hz (3 dB point) with an 8-pole Bessel low pass filter, and digitized at 1 kHz.

Light from light-emitting diodes with peak outputs at 470, 570, and 640 nm were combined using a trifurcated fiber optic and focused on the preparation using a water immersion lens in place of the microscope condensor. The light stimulus was spatially uniform and illuminated a circular area 0.57 mm in diameter centered on the recorded cell. Light intensities were measured at the preparation and converted to equivalent 500-nm photons (max for rod sensitivity) using the absorption spectrum of rhodopsin and the measured light-emitting diode spectrum.

Mouse Electroretinograms:

Mice were dark-reared from birth and anesthetized (ketaject/xylaject, 65 mg/kg intraperitoneally), and the pupils were dilated with tropicamide (1%). A contact lens electrode was placed on the eye with a drop of methylcellulose and a ground electrode placed in the ear. ERGs were recorded and analyzed with the universal testing and electrophysiologic system 3000 (UTAS E-3000) (LKC Technologies Inc., Gaithersburg, Md.). The mice were placed in a Ganzfield chamber, and flicker recordings were obtained from one eye. Flicker stimuli had a range of intensities (0.00040-41 cd·s/m$^2$) with a fixed frequency (10 Hz).

Immunocytochemistry:

Rpe65 mice were divided into five groups: Rpe65−/−, Rpe65−/− that were gavaged with 9-cis-retinal and kept in the dark; Rpe65−/− that were gavaged with 9-cis-retinal, exposed to a flash, and kept in the dark for 15 min; Rpe65+/+ that were kept in the dark; and Rpe65+/+ that were exposed to a flash and kept in the dark for 15 minutes. For the flash studies, dark-adapted mice were subjected to a flash (Sunpak 433D, 1 ms) from a distance of 2 cm. The retinas were fixed in 4% paraformalydehyde in 0.13 M sodium phosphate, pH 7.4, for 15 hours at 4° C., and the tissues were transferred to 5, 10, or 15% sucrose in 0.13 M sodium phosphate, pH 7.4, for 30 minutes each time and stored overnight in 20% sucrose in the same buffer at 4° C. The tissue was then transferred to optimal cutting temperature cryoembedding compound and sectioned at 10 μm. The cryosections were incubated overnight at 4° C. in mouse monoclonal anti-phosphorylated Rh A11-82P antibody diluted 1:10. Triton X-100 (0.1%) was included in all phosphate-buffered saline solutions to facilitate antibody penetration. The controls were processed by omitting primary antibodies from the incubation buffer. After incubation in primary antibodies, the sections were rinsed with phosphate-buffered saline and then incubated with indocarbocyanine (Cy3)-conjugated goat anti-mouse IgG (1:200). The sections were rinsed in phosphate-buffered saline mounted in 5% n-propylgallate in glycerol and coverslipped.

Results

Early Treatment with 9-Cis-Retinal Eliminates Oil-Like Structures in Rpe65−/− Mice:

In addition to the loss of photoreceptors, a defective interface between ROS and RPE, RPE cells of Rpe65−/− mice contained numerous lipid-like droplets. In young animals, empty vacuoles were observed in fixed electron microscopy sections of RPE from Rpe65−/− mice but not in controls. With increasing age (>PND 21), they were filled with a diffractive material that was retained during electron microscopy section preparation. This observation correlates with the excessive accumulation of all-trans-retinyl esters in Rpe65−/− mice (FIG. 1A, open circles). Retinyl esters also accumulated with age in Rpe65+/+ mice, albeit at lower levels than for Rpe65−/− mice. By PND 21, approximately 800 pmol/eye of retinyl esters accumulated compared with approximately 40 pmol/eye for Rpe65+/+. For Rpe65+/+ mice, rhodopsin levels initially exceeded the amount of retinyl esters several-fold.

Figure 1B:
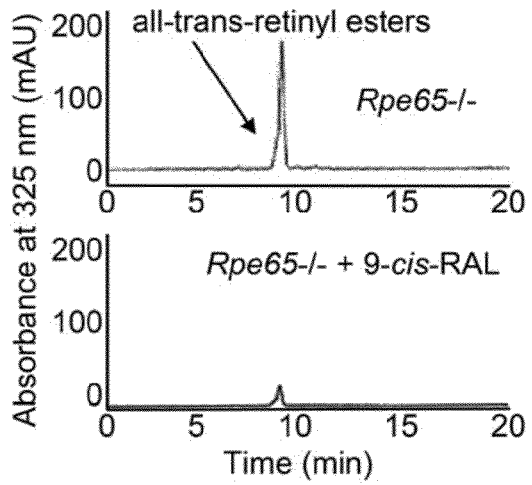
Figure 1C:
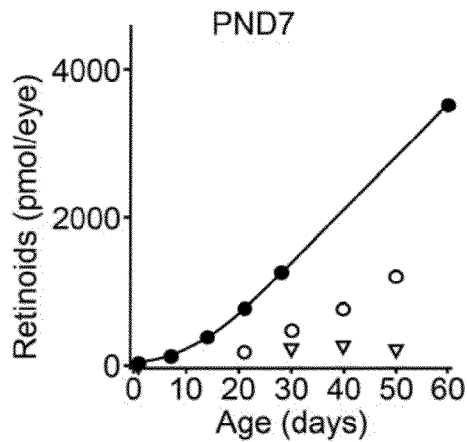
Figure 1C:
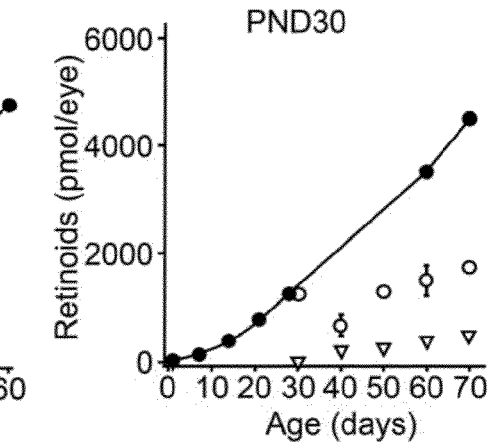
Figure 1D:
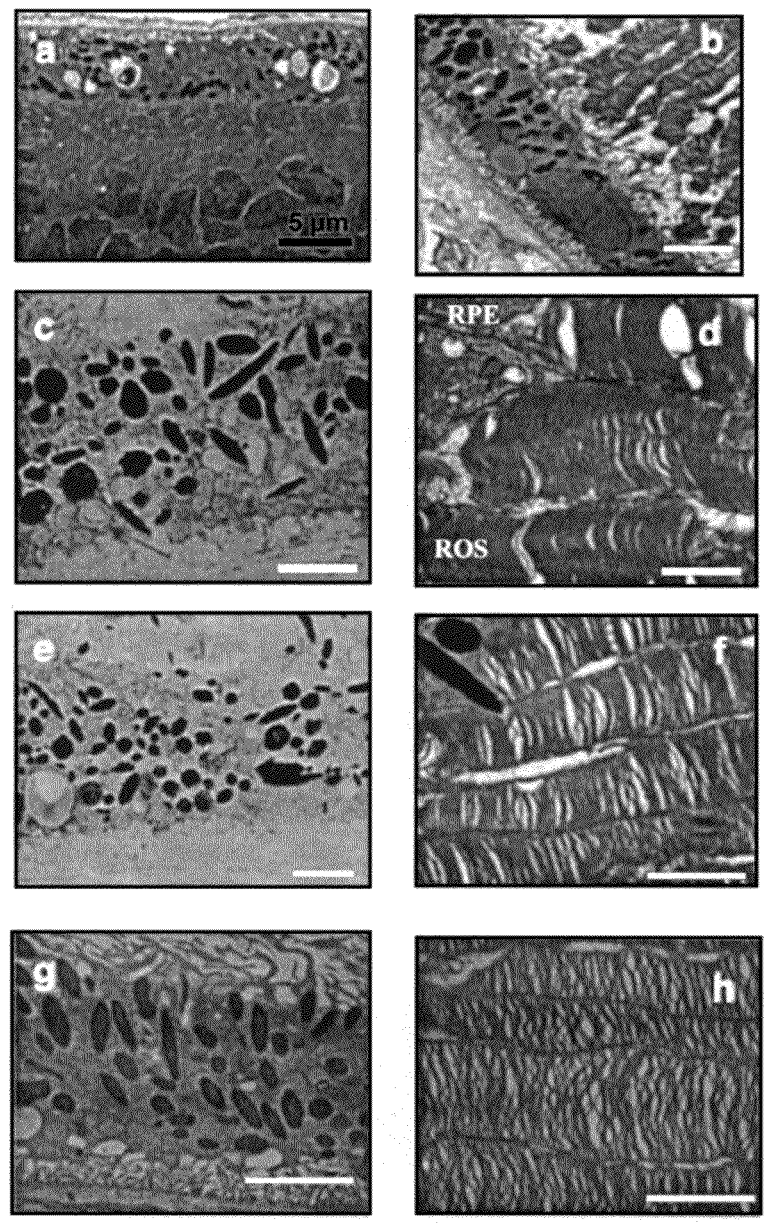

When PND 7 mice were treated with a 0.25-mg dose of 9-cis-retinal (10 mg/ml) every other day until they were 30 days old, a dramatic change in the ester accumulation was observed (FIG. 1B). With increasing age and continued administration of 1 dose (1.25 mg) per week, the amounts of all-trans-retinyl esters increased, similar to Rpe65+/+, but the overall amounts of esters were dramatically suppressed with concomitant formation of iso-rhodopsin (FIG. 1C, left panel). Once deposited, the accumulated esters in the RPE were not removed if the treatment began after more than 1 month of age (FIG. 1C, right panel). When young animals or young adults were treated with 9-cis-retinal, the interface contacts between the RPE and ROS were improved (FIG. 1D, panels d, f, and h), and the vacuoles appeared to be only partially filled (FIG. 1D, panels c and e) over several months of this study. These observations suggest that formation of the regenerated pigment significantly slowed down accumulation of esters, but did not promote the complete removal of the all-trans-retinyl esters that had been deposited in the eye.

Figure 2A:
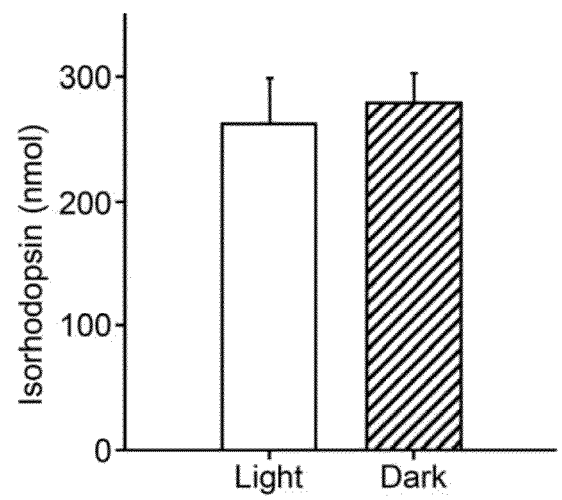
FIGS. 2A-2C. Effects of light exposure on iso-rhodopsin levels in Rpe65−/− mice gavaged 9-cis-retinal and ERG responses after a long term treatment with 9-cis-retinal.

Long Term Effect of 9-Cis-Retinal Treatment:

Treatment of mice with 9-cis-retinal produced a long lasting increase in photopigment levels and a decrease in accumulation of all-trans-retinyl esters. Rpe65−/− mice (1-month-old) were treated once (2.5 mg) with 9-cis-retinal and then kept under either a 12-hour light/dark cycle, or under 24 hour dark for 37 days. No appreciable depletion of retinal was observed under either set of conditions (FIG. 2A). These results suggest that a single dose of 9-cis-retinal sustains iso-rhodopsin in these animals under normal laboratory conditions.

Figure 2B:
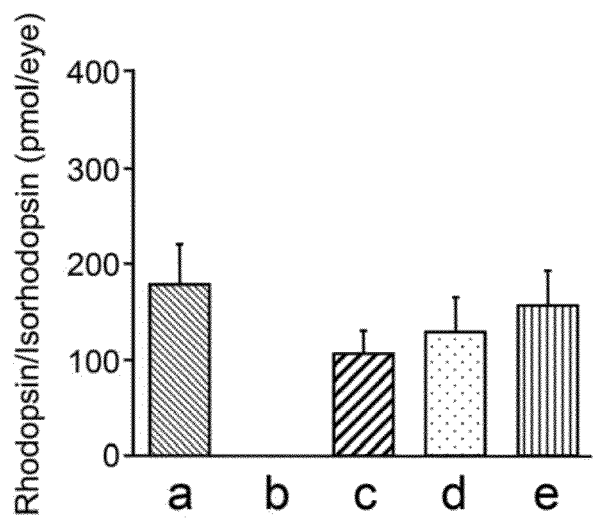

In another set of studies, the level of rhodopsin or iso-rhodopsin was measured in 6 month-old Rpe65−/− mice (FIG. 2B). In these animals, the iso-rhodopsin levels were comparable for three groups of Rpe65−/− mice: mice treated twice with 9-cis-retinal (2.5 mg/dose) at PND 30 and 34, mice treated twice at PND 30 and 120, and mice treated twice at PND 30 and 150. The 50% decrease of iso-rhodopsin in Rpe65−/− (FIG. 2, B compared with A) matches a similar decrease in rhodopsin in Rpe65+/+ as a function of age. The ester levels were reduced by >50% (compared with untreated animals) and were unaffected by the frequency and dose of 9-cis-retinal. No rhodopsin or iso-rhodopsin was detected in untreated dark-adapted Rpe65−/− mice.

9-cis-Retinal, reduced to 9-cis-retinol, can be stored in the eye and liver in the form of 9-cis-retinyl ester. When needed 9-cis-retinol would be liberated by a retinyl hydrolase. To determine how large the reservoir of 9-cis-retinoids is in the eye and liver, a group of mice were treated with 9-cis-retinal (2.5 mg) and after 48 hour exposed to multiple flashes at 1-hour intervals that bleached approximately 30-35% of rhodopsin/flash. iso-rhodopsin and 9cis-retinyl esters were significantly depleted after more than three intense flashes. Retinyl esters from liver and RPE were completely depleted after five flashes at 24-hour intervals. Continuous shedding and resynthesis of rhodopsin-containing ROS discs does not affect the long term preservation of the visual pigment. Therefore, it appears that 9-cis-retinal is, in a large part, recycled from phagocytized iso-rhodopsin to newly produced opsin molecules over an extended period of time.

Physiological Effects of 9-Cis-Retinal Treatment:

Treatment of Rpe65−/− mice with 9-cis-retinal also provided long term improvement of retinal function. The long term physiological effect of 9-cis-retinal treatment was determined from single flash responses of different intensities and flicker ERG measurements on Rpe65+/+ and Rpe65−/− mice. Previous studies showed a partial recovery of the ERG sensitivity 48 hours after oral 9-cisretinal administration. This partial recovery persisted for more than 12 weeks in Rpe65−/− mice treated once at PND 30.

Figure 2C:
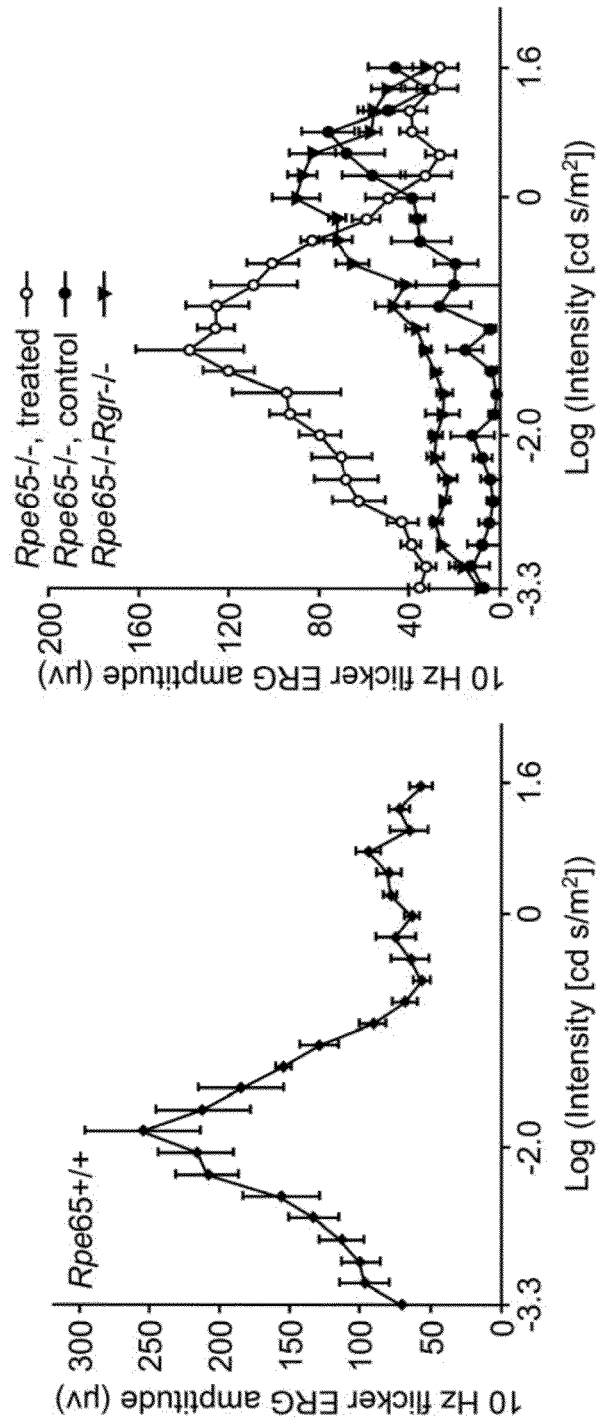

The flicker ERG in Rpe65+/+ mice reached a peak amplitude of 254.9±41.5 µV at a light level of 0.015 cd·s/m$^2$ and 95.1±8.9 µV at 7.5 cd·s/m$^2$ (FIG. 2C, left panel). These data resemble the rod and cone dominant ERG responses, respectively. In Rpe65−/− mice without treatment, the flicker ERG reached a significantly smaller peak amplitude, 76.0±12.0 µV, at a light level of 7.5 cd·s/m$^2$ (FIG. 2C, right panel). Eight weeks after a single treatment with 2.5 mg of 9-cis-retinal, the flicker ERG reached peak amplitudes of 137.3±24.4 µV at 0.059 cd·s/m$^2$ and 40.0±7.1 µV at 13 cd·s/m$^2$ (FIG. 2C, right panel). These peaks were smaller and occurred at a higher light level than in the Rpe65+/+ mice: however, the response of treated Rpe65−/− mice was 2.1 logarithmic units more sensitive and had larger amplitude than that of untreated mice. Thus, administration of 9-cis-retinal provided a long term, partial recovery of the ERG.

Treatment with 9-Cis-Retinal Eliminated Constitutive Opsin Phosphorylation:

To gain additional insight into the enzymatic processes of Rpe65 mice, several direct measurements of relevant enzymatic activities were carried out. It is generally accepted that opsin has some signaling capability. Immunolabeling on retina sections from Rpe65 mice using a monoclonal antibody against phosphorylated opsin could provide a clean evaluation of this activity, whereas it would be expected that 9-cis-retinal treatment would inhibit this activity.

The retinas from Rpe65+/+ mice and Rpe65−/− mice were fixed in constant darkness. The ROS in Rpe65+/+ mice showed no labeling, and the ROS from untreated Rpe65−/− mice were labeled by a monoclonal antibody against phosphorylated opsin. This labeling was abolished for Rpe65−/− mice (gavaged once at PND 30 and analyzed 48 hours post-treatment) treated with 9-cis-retinal. This 9-cis-treatment reduced phosphorylation of opsin to levels comparable with those in normal rods. ROS fixed in darkness at 15 minutes following a single flash showed immunolabeling in both Rpe65+/+ and Rpe65−/− mice treated with 9-cis-retinal. These data suggest that opsin is constitutively phosphorylated in Rpe65−/− mice. These studies indicated a specific deficit in conversion of all-trans-retinol to 11-cis-retinol and constitutive opsin phosphorylation but not in oxidation of 11-cis-retinol to 11-cis-retinal. Constitutive opsin phosphorylation could be an important element in the pathogenesis of LCA.

To directly measure the isomerase activity, RPE microsomes were isolated from Rpe65 mice using a novel procedure. In control studies using RPE microsomes from Rpe65+/+ mice, 11-cis-retinol was produced from exogenously added all-trans-retinol only in the presence of RPE microsomes and CRALBP. 11-cis-Retinol was absent when CRALBP was omitted, as well as when RPE microsomes or CRALBP were denatured by heat. 11-cis-Retinol was not detected in RPE microsomes from Rpe65-mice.

Because 11-cis-retinol dehydrogenase (1-cis-RDH) was purified in a complex with RPE65 protein, oxidation of 11-cis-retinol was investigated in RPE microsomes from Rpe65 mice. Strong activity was detected in Rpe65+/+ and Rpe65−/− mice using NADPH and NADH as a dinucleotide cofactor. To distinguish NADPH-dependent activity from NADH-dependent activity, the test for dehydrogenase activity was carried out in the presence of nonradioactive NADH and [$^3$H]NADPH. In such conditions, only NADPH-dependent dehydrogenase activity can be readily detected. The differences between Rpe65+/+ and Rpe65−/− were insignificant because this activity is much higher than required for normal flow of retinoids as determined from 11-cis-Rdh/mice (Jang et al., *J. Biol. Chem.* 276:3245665 (2001). These data suggest that RPE microsomes from Rpe65−/− mice contain high NADPH-dependent and NADH-dependent dehydrogenase activities. In addition, no differences were seen in immunolocalization of 11-cis-RDH in the RPE of Rpe65 mice.

Treatment with 9-Cis-Retinal Restores Normal Rod Function:

Because the ERG primarily reflects bipolar responses, the inability of 9-cis-retinal to provide complete recovery could be due to residual deficits in the photoreceptors or problems in signal transfer from rods to bipolar cells. To determine whether 9-cis-retinal treatment could restore normal photoreceptor function, suction electrodes were used to record the responses of single rods from Rpe65+/+ mice and untreated and treated Rpe65−/− mice (gavaged once at PND 30 and analyzed 48 hours post-treatment).

Light-evoked changes in circulating dark current were recorded from outer segments of single rods from Rpe65+/+ mice or Rpe65−/− mice gavaged 0, 0.25, 1.25, or 2.5 mg of 9-cis-retinal (once a day for two consecutive days preceding the study). Retinoid analysis revealed that 300±25 pmol of iso-rhodopsin/eye was formed with a 2.5 mg dose of 9-cis-retinal, 109.8 pmol of iso-rhodopsin/eye with a 1.25-mg dose, and 85.6±6.2 of pmol/eye with a 0.25-mg dose. The nonlinear relation between the dose of 9-cis-retinal and the iso-rhodopsin concentration presumably reflects accumulation in the liver and other tissues. All of the rod types listed supported light responses that increased with increasing flash strength to reach a maximum (saturating) amplitude when the light was bright enough to cause all of the cGMP channels to close and fully suppress the light-sensitive dark current of the cell. The response families from rods of each type show that the amplitude of the saturating response increases with increasing doses of 9-cis-retinal. The relationship between mean dark current for each group of rods and the dose of 9-cis-retinal is plotted. Light-sensitive dark current in Rpe65−/− rods that received no supplemental 9-cis-retinal was 2.1±0.3 pA, not significantly different from Rpe65−/− rods that received 0.25 mg of 9-cis-retinal (3.6±0.9 pA). Rod dark current increased with larger doses of chromophore, reaching a value that was essentially the same as Rpe65+/+ when mice where given 2.5 mg of 9-cisretinal.

Two other properties of the Rpe65−/− flash response varied with the amount of supplemental 9-cis-retinal, response kinetics and light sensitivity. To illustrate the kinetic differences, the average dim flash response (in the cells linear range) was determined for each rod type. The mean responses from the five different sets of rods were scaled to the same peak amplitude and compared. Responses recorded from Rpe65+/+ and Rpe65−/− rods from mice treated with 2.5 mg of 9-cis-retinal have essentially the same kinetics. The linear range responses are superimposed, showing that the dim flash responses of the two different rod types have the same time-to-peak and recovery times. Responses recorded from rods from Rpe65−/− mice gavaged with 1.25 or 0.25 mg of 9-cis-retinal are also essentially the same, with similar time-to-peak and recovery times; both are substantially faster than those of Rpe65+/+. The dim flash kinetics of rod responses from Rpe65−/− mice that received no supplemental 9-cis-retinal were intermediate; they were faster than Rpe65+/+ but slower than rods from mice treated with 1.25 or 0.25 mg of 9-cis-retinal.

Figure 3:
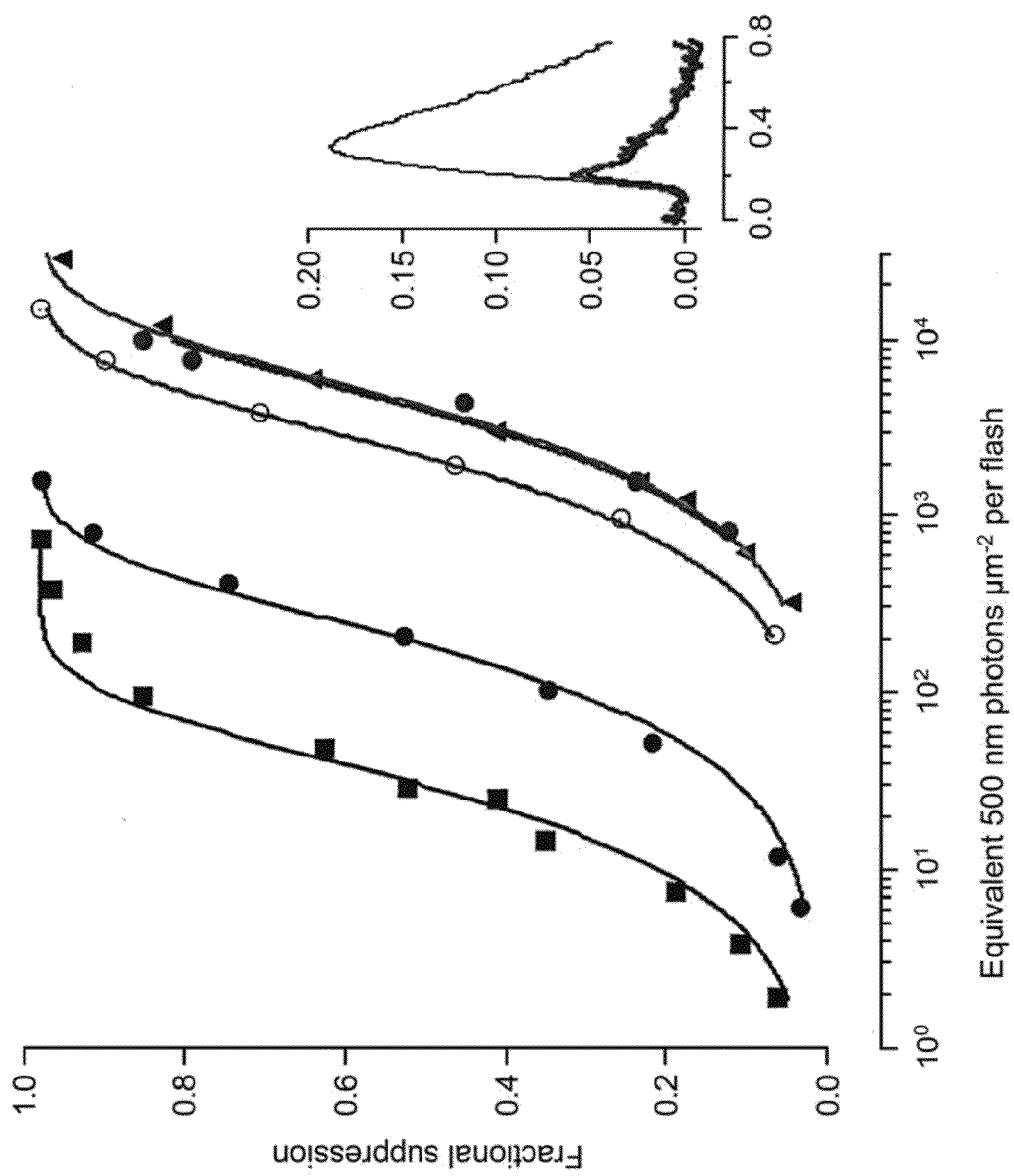
FIG. 3. Mean stimulus response curves (n=5) of Rpe6S+/+ (squares) and Rpe65−/− mice treated with 2.5 (filled circles), 1.25 (open circles), 0.25 (filled triangles), and 0 (filled circles on same line as filled triangles) mg of 9-cis-retinal. The differences in light sensitivity were evaluated by comparing the half-saturating flash intensity (10) obtained from fitting the mean data with an equation for exponential saturation.

The differences in light sensitivity between Rpe65+/+ rods and rods from Rpe65−/− mice are shown in FIG. 3, which plots the stimulus response curves for each of the five study conditions (Rpe65+/+ and Rpe65−/− mice gavaged with 2.5, 1.25, 0.25, or 0 mg of 9-cis-retinal). The half-saturating flash intensity was lowest in Rpe65+/+ rods (approximately 30 photons/$\mu m^2$) and increased by factors of 6, 66, and 131 in rods from mice gavaged with 2.5, 1.25, and 0.25 mg of 9-cis-retinal, respectively. The light sensitivity of rods from mice that did not receive 9-cis-retinal was the same as rods from mice that received the lowest dose (0.25 mg).

In the Absence of 9-Cis-Retinal Treatment, 11-Cis-Retinal is Produced in Rpe65−/− Mice by Photoisomerization:

Rpe65−/− mice that were never exposed to light have 11-cis-retinal (identified as oximes) below detection level in conventional microanalysis of retinoids. However, these mice respond to intense illumination in ERG studies and in single cell recordings. To identify whether 11-cis-retinal is produced by exposure to bright light, four or eight eyes were used for retinoid analysis instead of two eyes. For Rpe65−/−, no significant amounts of 11-cis-retinal were detected for dark-adapted animals. When more eyes were used for analysis, less than 0.2 pmol/eye of 11-cis-retinal oximes were detected in a typical chromatogram. All-trans-retinal (4.2±1.1 pmol/eye, n=8) was present, and an intense flash converted this aldehyde to 2.1±0.6 pmol/eye of 11-cis-retinal. The retinoids were identified by the retention time with authentic standards, and their UV spectra were measured during the chromatography. Next, it was important to determine whether photoisomerization resulted from the action of the "photo-isomerase" retinal G protein-coupled receptor protein. Double knockout Rpe65−/− Rgr−/− mice were generated, and retinoid analyses were carried out. A significant reduction in free all-trans-retinal was observed (2.2±0.2 pmol/eye), but light flash photo-converted a similar fraction (approximately 50%) to 11-cis-retinal. To identify where in the RPE or in the retina these retinals are present, retina and RPE were separated and analyzed individually (note that eight eyes were used). The majority of all-trans-retinal was observed in the retina, whereas 11-cis-retinal was present mostly in the RPE. Bleaching converted all-trans-retinal to 11-cis-retinal that also resided in the retina. Once 11-cis-retinal is formed, its level does not change after 15, 30, or 120 minutes in the dark.

The ERG analyses of Rpe65−/− Rgr−/− mice were not qualitatively different from the responses obtained from Rpe65−/− mice (FIG. 2C, right panel). Together, these results indicate that there is a retinal photoisomerization pathway that produces 11-cis-retinal and regenerates rhodopsin in prior bleached animals.

Different Methods of 9-Cis-Retinal Delivery:

An important point was to compare different ways to deliver 9-cis-retinoids with a goal to not only regenerate iso-rhodopsin but to also build up reservoirs of cis-retinoids. Two methods were tested: gavage (as described previously (Van Hooser et al., Proc. Natl. Acad. Sci. USA 97:8623-28 (2000)) and intravenous injections. Intravenous injection is an efficient way of delivering retinoids, and there were no major differences between aldehyde and alcohol forms or their isomeric compositions (11-cis-versus 9-cis-) of cis-retinoids. Intravenous injection of 9-cis-retinal produced iso-rhodopsin when delivered with and without cyclodextrins. Retinal was cleared out rapidly from the blood but could be stabilized in the circulation for a longer time in the presence of cyclodextrins (t1/2=12 hours versus 23 hours). The addition of cyclodextrin, possibly by extending the time of circulation, also led to higher accumulation of 9-cis-retinyl esters in the liver or RPE. A rapid clearance of 9-cis-retinal from the bloodstream makes it necessary to give multiple intravenous injections to fully regenerate iso-Rh. This is not the case with gavage, in which the presence of retinal in the bloodstream lasts for greater than 48 hours. Together, gavage and intravenous injections were effective in producing iso-rhodopsin in Rpe65−/− mice. The advantages and disadvantages of both methods are described under "Discussion" (infra).

Discussion

The Role of RPE65 and LCA: Although the sequence of events that lead to the diseased state in Rpe65−/− mice, the animal model of LCA, has not been established, it is likely that the primary defect is an interruption of the retinoid cycle. This cycle is responsible for regenerating the visual pigment through the enzymatic conversion of all-trans-retinal to 11-cis-retinal in the RPE and its return to the photoreceptor cell. Disruption of the normal retinoid flow between the RPE and photoreceptor can explain the overaccumulation of retinal esters in the RPE. Furthermore, the failure to regenerate rhodopsin can account for diminished rod and cone light sensitivity. The absence of 11-cis-retinal also increases free opsin in the photoreceptor. A high level of free opsin produces substantial activation of the phototransduction cascade, mimicking the effects of continuous light exposure. This ongoing activity may cause the reduction in the thickness of the ROS layer and photoreceptor degeneration, effects also produced in animals exposed to continuous light. This sequence of events may be further aggravated by the phosphorylation of free opsin, which has been shown in other studies to lead to retinal degeneration.

Early treatment of Rpe65−/− mice with 9-cis-retinal inhibited the accumulation of all-trans-retinal, improved the attachment contacts between RPE processes and ROS, led to dephosphorylation of opsin, and prevented the further progression of retinal degeneration. These observations suggest that ester accumulation in the RPE and the presence of high levels of active opsin in the photoreceptor may be the principle causes of retinal degeneration in the Rpe65−/− mouse.

Rescued Rod Function: The light sensitivity of rods from Rpe65−/− mice was restored in a dose-dependent manner by dietary supplemental 9-cis-retinal. The highest dose supported rod responses with normal sensitivity and kinetics. Treatment with lower doses of 9-cis-retinal gave rise to rod responses that were desensitized and had faster kinetics, closely resembling the changes in sensitivity and kinetics that occur during steady background illumination in wild-type rods. The changes in the light sensitivity of rod responses recorded from mice treated with the lower amounts of 9-cis-retinal could be accounted for by a combination of two factors. One source of desensitization was a decrease in the effective collecting area of the rod because of a reduction in both the amount of visual pigment and its quantum efficiency; the quantum efficiency of iso-rhodopsin is about one-third that of rhodopsin. The remaining reduction in sensitivity could be explained by steady activation of the transduction cascade by free opsin, producing an effect equivalent to that caused by steady background illumination in wild-type rods.

Rods from Rpe65−/− mice that were not treated with 9-cis-retinal also generated light responses that were strongly desensitized. The presence of residual rod responses in untreated Rpe65−/− mice is consistent with previous reports of reduced but present light responses in children with LCA. These results indicate that under these conditions the generation of light responses by flashes of intense light is most likely due to the production of 11-cis-retinal from the photoconversion of all-trans-retinal in the retina. It is open to speculation whether all-trans-retinal is free or coupled (either covalently or noncovalently) to opsin. The preassociation of the chromophore and opsin would make the formation of the light-sensitive 11-cis-retinal complex (i.e., rhodopsin) fast enough for it to be subsequently photoisomerized and transduction-triggered within the period of a brief (10 ms) flash of light.

Phototransduction in Rods of Rpe65 Mice:

The shifts in light sensitivity rods from treated and untreated Rpe65 mice can be attributed to a decrease in the effective collecting area of the rod acting either alone (2.5 mg of 9-cis-retinal) or in addition to desensitization by an "equivalent background" because of a low level of steady activation of the transduction cascade by free opsin.

The effective collecting area (ECA) depends on the geometric collecting area of the rod (A), the quantum efficiency of the pigment (QE), and the pigment density (α).

$$ECA = A QE \cdot (1 - 10^{\alpha l})$$ (Eq. 2)

where l is the path length. The pigment regenerated using 9-cis-retinal is iso-rhodopsin, which has about one-third of the quantum efficiency of Rh (0.22 versus 0.67). The biochemical measurements indicate that in mice gavaged with 2.5 mg of 9-cis-retinal, all of the pigment is iso-rhodopsin (no free opsin ±10%) and is about 57% of the amount of rhodopsin in Rpe65+/+ rods (i.e., 300 pM iso-rhodopsin versus 525 pM rhodopsin). The decreases in quantum efficiency and axial pigment density would be expected to cause approximately 5-fold decrease in effective collecting area of rods from mice fed with 2.5 mg of 9-cis-retinal. This is in agreement with the 6-fold increase in half-saturating flash strength in rods from Rpe65−/− mice gavaged with 2.5 mg of 9-cis-retinal, compared with rods of Rpe65+/+. In rods from mice treated with 1.25 and 0.25 mg of 9-cis-retinal, the axial densities of iso-rhodopsin were 21 and 16%, respectively, of the amount of rhodopsin in Rpe65+/+ rods. By the same reasoning as above, these changes would be expected to increase the half-saturating flash strength by 14.5- and 19-fold compared with Rpe65+/+. This is not enough to account for the observed shifts in sensitivity; rods from mice gavaged with 1.25 and 0.25 mg of 9-cis-retinal are further desensitized by factors of 4.5- and 6.8-fold, respectively.

The additional desensitization could be attributed to an equivalent background that acts like "dark light" to cause steady activation of the cascade. In separate studies on Rpe65+/+ rods the change in flash sensitivity by background illumination was described by the Weber-Fechner relationship:

$$S/S^d_f = 1/1 + I_b/I^o_b$$ (Eq. 3)

where $S_f$ is the flash sensitivity in steady light, S is flash sensitivity in darkness. $I_b$ is the background light intensity, and I is the background intensity (108 photons/$\mu m^2$/s) that reduces the flash sensitivity by half its dark value. Hence, background intensities of 378 and 648 photons/$\mu m^2$/s would be expected to cause 4.5- and 7-fold changes in flash sensitivity. With an effective collecting area of 0.5 $\mu m^2$ and an integration time of 0.3 seconds, these background intensities correspond to equivalent activation in Rpe65+/+ rods of 57 and 97 Rh*/s.

The equivalent background of residual free opsin was determined in the treated Rpe65−/− rods by combining biochemical measurements of the free opsin concentration with physiological estimates of desensitization. The number of Rh molecules in a Rpe65+/+ rod is estimated to be about $2 \times 10^7$ (i.e. 3 mM rhodopsin in 0.02 pl). Biochemical measurements on rods from Rpe65−/− mice indicate that they make approximately 40% less pigment than Rpe65+/+ 48 hours after treatment. Thus, the number of iso-rhodopsin molecules in rods from Rpe65−/− mice gavaged with 2.5 mg of 9-cis-retinal would be about $1.2 \times 10^7$. Smaller doses of 9-cis-retinal do not regenerate all of the available pigment to form iso-rhodopsin, causing there to be a pool of free opsin. The retinoid analysis suggests that the amount of free opsin in rods from Rpe65−/− mice gavaged with 1.25 and 0.25 mg of 9-cis-retinal would be 63 and 72% of the total amount of available pigment (i.e., $7.5-8.6 \times 10^6$ molecules). For this amount of free opsin to cause desensitization in the rods from Rpe65−/− mice that is equivalent to the desensitization in Rpe65+/+ rods caused by a steady light that bleaches 57 and 97 Rh*/s, about $1 \times 10^5$ opsin would have to activate the cascade as well as 1 Rh* ($1.3-0.9 \times 10^5$ opsin: Rh*). This value is broadly consistent with previous estimates of activation ratio of free opsin:Rh* (i.e., 106:1). The inset in FIG. 3 shows that background light adaptation and adaptation by an equivalent (free opsin) background that desensitized the flash response by similar amounts had similar effects on the kinetics of the dim flash response. This is also in general agreement with previous studies that showed the adaptational changes in the kinetics of the dim flash response were similar, whether adaptation was due to background light or the equivalent background associated with dark adaptation.

The highly desensitized rod responses recorded from untreated Rpe65−/− mice did not show the acceleration in response kinetics seen in rods from treated mice. There are several possible explanations for this difference. One possibility is that the activity of free opsin is less in rods from untreated Rpe65−/− mice than in those from treated mice, perhaps because of phosphorylation of the opsin in untreated rods. This explanation would require that treatment with a low dose of 9-cis-retinal converts most or all of the remaining free opsin to a state of higher activity, perhaps through dephosphorylation. Another possibility is that the activation and deactivation of the photopigment are altered in the untreated mice. For example, it is not clear that the photopigment created by photoconversion is identical to normal rhodopsin; for example, the opsin may still be phosphorylated.

The complete or nearly complete rescue of normal rod function after treatment with 9-cis-retinal contrasted with the partial rescue of the sensitivity of the electroretinogram. Because the electroretinogram primarily reflects activity of bipolar cells, this difference indicates that responses in the rods are not properly transmitted across the rod-bipolar synapse. It is possible this synapse does not develop properly in Rpe65-mice because of a lack of visual signals. Continuous treatment with 9-cis-retinal from birth may help remedy this problem.

Advantages and Disadvantages of 9-Cis-Retinal Treatments:

Retinals can be delivered to the eye effectively by one (or a combination) of two methods: gavage and intravenous injection. The most effective delivery system is gavage, which restores visual pigment in 1-2 days and also produces accumulation of 9-cis-retinyl esters in the liver and RPE microsomes. It is a highly reproducible procedure. There is a transient elevation of retinoids in the blood for 48 hours that is followed by recovery to the normal level. The only noticeable drawback is that much of the retinoid is secreted rather than stored, requiring a higher dose than other delivery methods.

Intravenous injection is also an effective method for retinoid delivery to the eye, but it has the disadvantage of the retinoids being rapidly eliminated from the bloodstream by the kidneys. This can be prevented to some degree by "caging" retinal in a cyclodextrin net. For full regeneration, multiple or large doses must be injected, causing potential problems with local infection. To lower the amounts of circulating all-trans-retinoids, it would be helpful to inhibit liver carboxylesterase to prevent all-trans-retinal from being released to the bloodstream. Such inhibitors, if they are potent, are highly toxic, because they inhibit other processes that require hydrolase activity. General and mild inhibitors, such as vitamins $K_1$ and E, are effective to some degree, but more specific inhibitors are needed to enhance the level of cis-retinoids in the bloodstream. Finally, intraocular injection is an option in same cases.

There is not a large reservoir of cis-retinoids in the liver and RPE, most likely because of nonenzymatic conversion of free retinal or retinol to the all-trans isomer. However, the efficiency of mammalian vision is remarkable and worth consideration in light of cis-retinoid therapy. For example, the mammalian retina contains approximately 108 photoreceptors. If each photoreceptor absorbs on average $1-2 \times 10^3$ photons/s, with a quantum yield of 0.65 (or 0.3 for 9-cis-retinal), the daily requirement of 11-cis-retinal is only less than 1 µg, an amount that could be easily delivered by dietary supplement even if the majority of retinoids are retained in liver or secreted. The recommendations for vitamin A intake is 0.8 mg/day for men and 0.7 mg/day for women, with the upper safety limit of 3 mg/day is only an estimate, because of lack of data.

Multiple gavages do not increase the amount of retinyl esters in the eye. In contrast, early intervention significantly lowers the accumulation of all-trans-retinyl esters (FIG. 1). This could be one of the prerequisites of successful cis-retinoid therapy for retinal diseases. The level of all-trans-retinyl esters in the RPE is predetermined by the time of the intervention. If the treatment is initiated very early in life, the esters only gradually increase with age, as in wild-type mice. The treatment does not remove the esters from the eye but prevents accumulation of the esters. One possible explanation is that the retina sends a signal that opsin is not regenerated, and this causes retinol capture from the blood circulation and retention as retinyl ester in RPE. When retinyl esters cannot be converted to 11-cis-retinal, and the "opsin signal" is on, these two factors ultimately lead to ester accumulation. The mechanism of such communication is unknown on a molecular level.

In summary, this study provides evidence that administration of 9-cis-retinal restores rod photopigment and rod retinal function for more than 6 months and that early intervention significantly attenuates the ester accumulation. Opsin in Rpe65−/− mice is constitutively phosphorylated in rods of Rpe65−/− mice, and this modification of the visual pigment could be involved in the pathophysiology of LCA: fortunately, after 9-cis-retinal-treatment, opsin is dephosphorylated. Evidence is also provided that the source of 11-cis-retinal in Rpe65−/− mice results from photoisomerization of all-trans-retinal present in the retina and that other mechanisms in addition to photoisomerase retinal G protein-coupled receptor are involved in this process, as shown in double Rpe65−/− Rgr−/− knockout mice. Electrophysiological data using single cell recordings suggest that 11-cis-retinal is formed in situ in rod outer segments. These studies provide information about the etiology of LCA on a molecular level and demonstrate that pharmacological intervention produces long lasting preservation of the visual function in dark-reared Rpe65−/− mice.

Example 2

Phototransduction is initiated by the photoisomerization of rhodopsin (Rh) chromophore 11-cis-retinylidene to all-trans-retinylidene. Here, using rhodopsin regenerated with retinal analogs with different ring sizes, which prevent isomerization around the C11=C12 double bond, the activation mechanism of this G-protein-coupled receptor was investigated. 11-cis-7-ring-rhodopsin does not activate G-protein in vivo and in vitro, and it does not isomerize along other double bonds, suggesting that it fits tightly into the binding site of opsin. In contrast, bleaching 11-cis-6-ring-rhodopsin modestly activates phototransduction in vivo and at low pH in vitro. These results reveal that partial activation is caused by isomerization along other double bonds in more rigid 6-locked retinal isomers and protonation of key residues by lowering pH in 11-cis-6-ring-rhodopsins. Full activation is not achieved, because isomerization does not induce a complete set of conformational rearrangements of rhodopsin. These results with 6- and 7-ring-constrained retinoids provide new insights into rhodopsin activation and indicate a use of locked retinals, particularly 11-cis-7-ring-retinal.

In vertebrate retinal photoreceptor cells, isomerization of the visual pigment chromophore, 11-cis-retinal to all-trans-retinal, triggers a set of reactions collectively termed the phototransduction cascade. The phototransduction events are initiated by activated rhodopsin (Rh*) and progress through a classical G-protein cascade, ultimately leading to neuronal signaling. Metarhodopsin II (or Meta II, Rh*), the catalytically active intermediate generated by photoisomerization of rhodopsin chromophore, contains all-trans-retinal covalently bound to Lys296 of opsin via the deprotonated Schiff's base. Subsequently, Meta II undergoes reprotonation, and the photolyzed chromophore is hydrolyzed and released from opsin. The precise mechanism of rhodopsin activation by the photoisomerized chromophore is unknown.

The photobleaching process of rhodopsin has been investigated using retinal analogs that contained an extra ring between C10 and C13, making retinal non-isomerizable around the 11-cis double bond. An artificial visual pigment with restricted C9=C11 motion forms normal photolysis intermediates, suggesting an importance of C11=C12 bond isomerization in the activation of rhodopsin. More recently, it was reported that after photoisomerization, the β-ionone ring of the chromophore moves to a new position during the transition to Meta II (Borhan et al., *Science* 288:2209-12 (2000)). Jang et al. (*J. Biol. Chem.* 276:26148-53 (2001) showed using 6-ring-constrained retinal isomers and the crystal structure of rhodopsin in the ground state that if this movement is restricted, only residual activity could be observed. Locked retinal analogs have also used to study visual transduction in vivo using vitamin A-deprived rats. These animals had approximately half of the normal complement of rhodopsin, and injection of locked retinal led to the appearance of the analog pigment in the photoreceptors but without significant effect on the sensitivity of electroretinographic b-wave responses recorded from rat eye. Interference from wild-type rhodopsin prevented full interpretation of the results.

The light-triggered events in photoreceptors are intimately intertwined with the regeneration reactions that involve a two-cell system, photoreceptor cells and the retinal pigment epithelial cells (RPE). Every photoisomerization caused by absorption of a photon is counterbalanced by regeneration of rhodopsin with newly synthesized 11-cis-retinal. The photoisomerized product all-trans-retinal released from Rh* is reduced to all-trans-retinol in photoreceptors and then converted back to 11-cis-retinal in the RPE in an enzymatic process referred to as the visual cycle or the retinoid cycle (McBee et al., *Prog. Retin. Eye Res.* 20:469-529 (2001). Several components of the retinoid cycle have been identified, although major enzymatic and chemical transformations still remain poorly understood.

One of the proteins involved in the retinoid cycle is RPE65, a highly expressed membrane-associated RPE protein with a molecular mass of 65 kDa. This protein appears to form a complex with 11-cis-retinol dehydrogenase (11-cis-RDH). The function of RPE65 is unknown, but it is believed to be involved in retinoid processing. RPE microsomes washed with high salt that removed greater than 95% RPE65 still retained most of the isomerization activity. However, unexpectedly, Rpe65−/− mice had an overaccumulation of all-trans-retinyl esters in the RPE in the form of lipid-like droplets. Further retinoid analysis revealed no detectable 11-cis-products in either ester or alcohol forms. Electroretinogram (ERG) measurements of Rpe65−/− mice revealed that the rod and cone functions were severely attenuated. Small amounts of 11-cis-retinal are produced by photochemical reaction in situ in photoreceptor cells, and it was demonstrated that early intervention with cis-retinoids greatly attenuates retinyl ester accumulation (see Example 1). This animal model is very useful for studying in vivo properties of rhodopsin regenerated with synthetic retinal analogs that undergo photoactivation processes differently from 11-cis-retinal without interference from wild-type rhodopsin.

In this study, rhodopsin, regenerated with ring-constrained 11-cis-retinal isomers and containing a 3-carbon bridge between C10 and C13 that prevents isomerization around the C11-C12 double bond, does not undergo significant isomerization and activation in vivo or in vitro. In contrast, the bleaching of 11-cis-6-ring-rhodopsin (2-carbon bridge) leads to isomerization along both double bonds and produces active species of rhodopsin at low pH that trigger phototransduction events in vivo and in vitro as demonstrated by FTIR spectroscopy. These results provide new insights into rhodopsin activation and concurrently indicate that 6- and 7-ring-constrained retinoids will be useful in retinoid therapy for retinal pathologies.

Methods and Materials

Synthesis of 11-Cis-7-Ring-Retinals:

11-cis-7-ring-retinals were synthesized according to published procedures (Akita et al., *J. Am. Chem. Soc.* 102:6372-6376 (1980); Fujimoto et al., *Chirality* 14:340-46 (2002); Caldwell et al., *J. Org. Chem.* 58:3533-37 (1993)). (See FIG. 4A for the identification of isomers 1-4, also referred to as compounds 1-4.)

Photoisomerization of Rhodopsin Regenerated with 11-Ccis-7-Ring-Retinals:

Preparation of rod outer segment, opsin, rhodopsin regeneration with retinals, and purification of rhodopsin on a concanavalin A-Sepharose 4B column were conducted as described previously (Jang et al., *J. Biol. Chem.* 276:26148-53 (2001)).

Phosphorylation of Rhodopsin Regenerated with 11-Cis-Retinal and 11-Cis-7-Ring-Retinals:

Regenerated rhodopsin (2 mg/ml) was mixed in 100 μl of 100 mM sodium phosphate buffer, pH 7.2, containing 5 mM $MgCl_2$, 0.5 mM [$^{32}P$]ATP (approximately 35,000 to approximately 50,000 cpm/nmol) and purified rhodopsin kinase (approximately 5 μg of protein), and the assay was carried out as described previously (Palczewski et al., *J. Biol. Chem.* 266: 1294955 (1991)). Studies were performed in triplicate.

HPLC Activity Assay for RDI with 11-Cis-7-Ring-Retinal Isomers:

Activities of 11-cis-RDH (retinol dehydrogenase) and photoreceptor all-trans-retinal-specific RDH (prRDH) or all-trans-RDH were assayed by monitoring the production of [15-$^3H$]retinol isomers (reduction of retinal isomers) (Jang et al., *J. Biol. Chem.* 275:21128-38 (2000)). The reaction mixture (100 μl) contained MES (final concentration, 66 mM, pH 5.5), 1 mM DTT, pro-S-[4-$^3H$]NADH (16 μM) for purified 11-cis-RDH-His6 (0.31 μg), (Jang et al., *J. Biol. Chem.* 275: 21128-38 (2000)) or pro-S-[4-$^3H$]NADPH (12 μM) for prRDH (expressed in Sf9 cells and suspended in 20 mM BTP, 1 mM dithiothreitol, 1 μM leupeptin at a 1:49 cell pellet/buffer ratio), and 2 μl of 11-cis-7-ring-retinal isomer (120 μM) substrate stock added last to initiate the reactions. The reactions were incubated at 33° C. for 10-20 minutes.

Lecithin: Retinol Acyltransferase (LRAT) Assay:

Fresh bovine eyes were obtained from Schenk Packing Co., Inc. (Stanwood, Wash.). Preparation of bovine RPE microsomes was described previously (Stecher et al., *J. Biol. Chem.* 274:8577-85 (1999)). The microsomes were resuspended in 10 mM MOPS, 1 μM leupeptin, and 1 mM dithiothreitol to a total protein concentration of approximately 5 mg/ml as determined photocolorimetrically (Bradford, *Anal. Biochem.* 72:248-54 (1976)). Aliquots were stored at 80° C. and were used within 1 month of preparation. To destroy endogenous retinoids, 200 μl of aliquots of RPE microsomes were irradiated in a quartz cuvette for 5 minutes at 0° C. using a ChromatoUVE-transilluminator (model TM-15 from UVP Inc.). All studies were carried out under dim red light conditions. All-trans-retinol, 11-cis-retinol, and 11-cis-7-ring-retinols were dissolved in dimethylformamide to 1 mM concentration as determined spectrophotometrically. To a 1.5-ml polypropylene tube containing 130 μl of 10 mM BTP, pH 7.4, 20 μl of 10% bovine serum albumin, and 10 μl of 10 mM ATP (in mM BTP (1,3-bis[tris(hydroxymethyl)-methylamino] propane), pH 7.4) was added 20 μl of UV-treated bovine RPE microsomes (approximately 100 μg of total protein). 2 μl of 1 mM dimethylformamide solution of 11-cis7-ring-retinol then was added to the mixture and incubated at 37° C. for the indicated times. The reactions were quenched by the addition of 300 µl of MeOH and 300 µl of hexane. Retinoids were extracted by vigorous shaking on a vortex for 5 minutes and then centrifuged at 14,000 rpm for 4 minutes to separate hexane and aqueous layers. The hexane extract (100 µl) was analyzed by a normal phase HPLC (4% ethyl acetate/hexane). The studies were performed in duplicate, and the amount of retinoids was normalized.

LRAT Inhibition Assay:

The assay was performed as described above, but after preincubation with 11-cis-7-ring-retinols for 15 minutes at 37° C., 2 µl of 1 mM solution of all-trans-retinol or 11-cis-retinol was added, and reactions were incubated for an additional 10 minutes. For control, the reactions were preincubated with 2 µl of dimethylformamide without 11-cis-7-ring-retinols.

FTIR Spectroscopy:

Opsin membranes (24 µM) (Sachs et al., *J. Biol. Chem.* 275:6189-94 (2000)) were incubated overnight with 240 µM 11-cis-retinal or with the mixture of either 11-cis-6-ring- or 11-cis-7-ring-retinal isomers in the BTP buffer (20 mM BTP, pH 7.5, containing 1 mM MgCl2 and 130 mM NaCl). Suspensions of membranes were centrifuged for 25 minutes at 100,000×g and resuspended in the BTP buffer to yield 2.2 mM rhodopsin (from absorption at 500 nm). For the measurements with the high affinity analog of transducin (Gt)-(340-350), 8 mM VLEDLKSCGLF (SEQ ID NO:1) was used. For $H_2O/D_2O$ exchange, the pellet was resuspended three times in deuterated buffer. The buffer solution was removed, and the pellet transferred to a 30-mm-diameter temperature-controlled transmission cell with two $BaF_2$ windows and a 3 µm polytetrafluoroethylen gasket. The spectra were recorded using a Bruker ifs 66-V spectrometer (Bard et al., *FEBS Lett.* 473:259-64 (2000)). For all samples, Meta II minus rhodopsin difference spectra were produced.

Kinetic Light Scattering.

Light-scattering changes were measured as previously described (Heck et al., *Methods Enzymol.* 315:32947 (2000)). Measurements were performed in 10-mm path cuvettes with 300-µl volumes in isotonic buffer (20 mM BTP, 130 mM NaCl, and 1 mM $MgCl_2$, pH 6.4, as indicated in the legend to FIG. 6) at 22° C. with a 5-ms dwell time of the A/D converter (Nicolet 400, Madison, Wis.). Samples contained membrane suspension (3 µM rhodopsin) reconstituted with purified Gt (0.8 µM) and 1 mM GTP. Reactions were triggered by flash photolysis of rhodopsin with a green (500±20 nm) flash attenuated by appropriate neutral density filters. The flash intensity was quantified photometrically by the amount of rhodopsin bleached and expressed in terms of the mole fraction of photoexcited rhodopsin (Rh*/Rh).

Animals:

All animal studies employed procedures approved by the University of Washington Animal Care Committee and conformed to recommendations of the American Veterinary Medical Association Panel on Euthanasia. All animals were maintained in complete darkness, and all manipulations were done under dim red light employing a Kodak No. 1 Safelight filter (transmittance >560 nm). Typically, 2-3-month-old mice were used in all studies. RPE65-deficient mice were obtained from M. Redmond (National Eye Institute, National Institutes of Health. Bethesda, Md.) and genotyped as described previously (Redmond et al., *Nat. Genet.* 20:344-51 (1998; Redmond et al. *Methods Enzymol.* 316:705-24 (2000)).

Analyses of Retinoids and Visual Pigments:

All procedures were performed under dim red light as described previously (Van Hooser et al., *Proc. Natl. Acad. Sci. USA* 97:862328 (2000); Jang. et al., *J. Biol. Chem.* 276:3245665 (2001); Palczewski et al., *Biochemistry* 38:12012-19 (1999)).

ERGs:

Mice were anesthetized by intraperitoneal injection with 15 µl/g body weight of 6 mg/ml ketamine and 0.44 mg/ml xylazine diluted with 10 mM phosphate buffer, pH 7.2, containing 100 mM NaCl. The pupils were dilated with 1% tropicamide. A contact lens electrode was placed on the eye with a drop of methylcellulose, and a ground electrode (a reference electrode) was placed in the ear. ERGs were recorded with the universal testing and electrophysiologic system 3000 (UTAS E-3000) (LKC Technologies, Inc.). The mice were placed in a Ganzfield chamber, and responses to flash stimuli were obtained from both eyes simultaneously. Flash stimuli had a range of intensities (0.00020-41 candela $s/m^2$), and white light flash duration was 10 ms. Two to four recordings were made with >10-second intervals. Typically, 4-8 animals were used for recording of each point in all conditions. All ERG measurements were done within 10-40 minutes after anesthesia.

Immunocytochemistry:

The section preparation and immunolabeling using anti-phosphorylated rhodopsin antibody, A1182P (a generous gift from P. Hargrave), were carried out as described previously (Van Hooser et al., *J. Biol. Chem.* 277:19173-82 (2002)).

Modeling:

Coordinates for bovine rhodopsin were taken from the Protein Data Bank (1HZX). An addition of hydrogen atoms and all optimizations were done in Insight II (InsightII release 2000. Accelrys Inc, San Diego, Calif.) as described previously (Jang. et al., *J. Biol. Chem.* 276:26148-53 (2001)).

Results

Synthesis of 11-Cis-7-Ring-Retinals and Modeling of the Active Site of Rhodopsin:

The total synthesis of 11-cis-locked retinal analog incorporating a 7-membered ring was recently reported (Fujimoto et al., *Chirality* 14:340-46 (2002)). This method was followed with modifications to synthesize 11-cis-7-ring-retinals. The compound was prepared as a mixture of four isomers. These isomers are well separated by normal phase HPLC and have UV-visible and $^1$H NMR spectra identical to those described earlier under "Methods and Materials" (supra) (Caldwell et al., *J. Org. Chem.* 58:3533-37 (1993); Akito et al., *J Am Chem. Soc.* 102:6370-72 (1980)). The conformation of isomer 3,11-cis-7-ring-retinal, overlaps to a high degree with 11-cis-retinal. All isomers fit into the binding site of rhodopsin as demonstrated by molecular modeling using the x-ray structure of rhodopsin (Palczewski et al., *Science* 289:739-45 (2000); Teller et al., *Biochemistry* 40:7761-72 (2001)) and energy minimization algorithms.

Susceptibility of 11-Ccis-7-Lock-Rhodpsin to Isomerization, Reduction, and Esterification:

11-cis-7-Ring-retinals are more stable to thermal isomerization compared with 6-ring isomers. Bleaching these 7-ring-retinoids in solution produces a mixture of isomers with the least abundant isomer being 9,11,13-tricis-retinal 1 (FIG. 4A). Rhodopsin regenerated with these isomers was purified using concanavalin A column chromatography (FIG. 4B). When bound to opsin, 11-cis-7-ring-retinal (isomer 3) appears to be most stable to isomerization (FIG. 4C), whereas 11,13-dicis isomer 2 converts readily to isomer 3 even in the dark, suggesting that opsin promotes this isomerization. Overall, 7-ring-containing retinoids appear to be more stable in all conditions and undergo interconversion to a lower degree compared with 6-ring-containing retinals. With the exception of the tri-cis isomer 1, they are poor substrates for 11-cis-RDH. They are utilized by prRDH without discrimination among different isomers. These data again are different from 6-ring-retinoids. The activities of both dehydrogenases for the best substrates are only approximately one-tenth of that of native retinals, suggesting that these substrates will be poorly utilized by dehydrogenases endogenous to the visual system. These retinoids are also poor substrates for LRAT, and only a fraction can be esterified (FIG. 5). 11-cis-7-Ring-retinals are ineffective inhibitors of LRAT when assayed in the presence of all-trans-retinol or 11-cis-retinol as substrates.

Activity of 11-Cis-7-Ring-Rhodopsin In Vitro:

To assess the light-induced transformation in rhodopsin regenerated with 11-cis-7-ring-retinals, FTIR spectroscopy was employed to monitor spectral changes characteristic to different regions of opsin. Upon photoactivation, rhodopsin regenerated with isomers 1 and 4 yielded only minor changes in the difference spectra compared with wild-type rhodopsin, whereas isomers 2 and 3 were inactive. These changes reflect isomerization around other double bonds, excluding the locked C11=C12 double bond because the 11-cis-bond is locked. All of these spectra were pH-insensitive, FTIR reveals that the chromophore is changing its geometry upon bleaching, but the movements of the chromophore do not cause significant changes in hydrogen bonding or in protonation states of carboxylic acids of rhodopsin. Consistent with the spectral data, light-scattering changes as a monitor of Gt activation yielded exceedingly low but measurable pH-independent activity.

In Vivo Regeneration of Rhodopsin with 6- and 7-Ring Isomers:

To produce rhodopsin regenerated with retinoid analogs for in vivo studies, Rpe65 mice were generated by Redmond et al. (24). These mice are unable to produce substantial amounts of 11-cisretinal (Van Hooser et al., *Proc. Natl. Acad. Sci. USA* 97:8623-28 (2000)). Rhodopsin in Rpe65+/+ mice has a chromophore that is light-sensitive. However, rhodopsin regenerated with 11-cis-7-lock-retinals in vivo employing Rpe65−/− mice produced light-insensitive rhodopsin that could be detected in the difference spectra by the addition of 1% SDS. The retinoid analysis revealed the presence of the expected amount of visual pigment. Although the injection of the mixture of 7-ring isomers yielded only one isomeric product (11-cis-7-ring-retinal, isomer 3), the mixture of 6-ring-containing retinal produced three isomers as could be predicted from previous work (Jang. et al., *J. Biol. Chem.* 276: 26148-53 (2001)). These results suggest that opsin is readily and preferentially regenerated in vivo with 11-cis-7-ring-retinal, which mimics the structure of 11-cis-retinal.

Lack of Activity for 11-Cis-7-Ring-Rhodopsin In Vivo:

To increase the sensitivity of the assay and to assess the properties of rhodopsin regenerated with 7-lock isomers in vivo, Rpe65−/− mice were treated with isomer 3. The activity (a- and b-wave) was unaffected by the treatment as compared with samples with only Me$_2$SO. In contrast, in a positive control, 9-cis-retinal significantly increased sensitivity of treated mice, even at low light intensities. Furthermore, 11-cis-7-ring-rhodopsin was inactive in vitro in the phosphorylation assay using purified rhodopsin kinase.

In summary, these results demonstrate that 7-ring-retinal produces rhodopsin, which for the most part is inactive in all tested conditions. This finding was confirmed using complementary methods of different sensitivities in vivo and in vitro such as FTIR, ERG, Gt activation, and phosphorylation as detection assays.

11-Cis-6-Ring-Rh Is Active In Vivo and In Vitro:

Surprisingly, rhodopsin regenerated in vivo with 6-ring-containing retinal is active at higher bleaches. The a- and b-waves are clearly elevated compared with the Me$_2$SO control. This result is consistent with the minor activity of rhodopsin as previously measured (Bhattacharaya et al., *J. Biol. Chem.* 267:6763-69 (1992); Ridge et al., *J. Biol. Chem.* 267:6770-75 (1992): Jang. et al., 276:26148-53 (2001)). The relative activity of rhodopsin and the pigments with locked analogs is as follows. With membranes containing rhodopsin regenerated with 6-locked analogs, a 1350-fold intensity of the activating light flash is needed to evoke Gt activation rates comparable to wild-type rhodopsin. Consistent with the pH dependence observed in the FTIR, spectra, the activity is enhanced at acidic pH. This is in contrast to the well known pH/rate profile of native rhodopsin (higher activity at pH 7.4 as compared with pH 6.4). Besides the mechanistic implications of this result (see "Discussion," infra), these data allow the exclusion of the idea that the activity of the locked analogs is merely because of trace amounts of endogenous 11-cis-retinal. Moreover, the activity of rhodopsin regenerated with 6-locked analogs is sensitive to hydroxylamine, indicating a similar "open" conformation of the light-activated photoproduct as compared with native Rh*. Consistent with the findings in vivo, the activity of 11-cis-6-ring-rhodopsin is markedly higher than that of the 7-locked pigment.

The FTIR spectra indicate different protein-chromophore interactions of the ground state of 11-cis-6-ring-rhodopsin compared with the bleached sample. At pH 7.5, the change in chromophore-protein interaction, indicated by a band at 1206 cm$^{-1}$, did not lead to significant changes in the protein, and only residual activity could be detected (14). However, at pH 4.5, the same movements led to reorientation of hydrogen bonds and changes in secondary structure, forming a Meta II-like product that is able to bind Gt-(340-350) derived peptide. This finding suggests that pH induces structural changes in opsin that render possible the interaction of the chromophore with the protein environment in the binding site. The pK$_a$ for this change is 5.4 and the Meta II-like structure decays with a half-width time comparable to Meta II regenerated with 11-cis-retinal. A band at 1713 cm$^{-1}$ in the Rho/ Meta II difference spectrum assigned to the protonation of Glu113 appears to be shifted to 1708 cm$^{-1}$ in the Meta II-like product regenerated with 11-cis-6-ring isomer at pH 4.5. In contrast to the Meta II band at 1713 cm$^{-1}$, this band is not shifted significantly when the sample is treated with D$^2$0, but the bond shape has slightly changed. Interestingly, this band is still observed in the Meta 11-like photoproduct of the E113Q mutant of rhodopsin regenerated with 11-cis-6-ring isomer.

Discussion

The results of this study lead to conclusions on two different although related topics, namely the mechanism of activation of rhodopsin and the utilization of the retinoid analogs in vivo.

Rhodopsin Activation: New Lessons Learned from the Studies of Retinoid Analogs:

This study revealed new important information on the activation process. Three sharply distinct classes of the chromophore-protein interaction were found for 11-cis-7-ring- and 11-cis-6-ring-containing retinals and 11-cis-retinal. 1) Rhodopsin regenerated with 11-cis-7-ring isomer has only 0.10% of wild-type activity; it is also inactive in both sensitive ERG and FTIR studies. This low activity could be a result of the presence of a small amount of free opsin and consistent with the estimated activation ratio of free opsin:Rh*, i.e. 10$^6$:1. Therefore, it appears that 11-cis-7-ring-retinal is stabilized by the opsin binding pocket, forming stable 11-cis-7-ring-rhodopsin. The bleaching of 9,11-dicis and 9,11,13-tricis results in a conversion to the most stable isomer, isomer 3, and FTIR spectra that are consistent with the lack of Gt activation. 2) In contrast, the possible movements of 11-cis-6-ring-retinal along C9=C10 and C13=C14 double bonds are sufficient to overcome the trigger bather in the activation of rhodopsin. This activity can be clearly detected in vivo and in the light-scattering assays, advancing previous measurements using nucleotide uptake and phosphorylation assays. This active state resembles Meta II in its sensitivity to hydroxylamine, in features of the FTIR spectrum, and in its interaction with Gt peptide. However, the bleaching of 11-cis-6-ring-Rh leads to a Gt activation that is pH-dependent, whereas Meta II has a broad high activity over a wide range of pH values. This result suggests that isomerization along C9-C10 and C13-C14 causes sufficient relaxation of rhodopsin around the chromophore to allow activation as was observed for chromophore-free opsin. However, the activation of the rhodopsin is not achieved with proper "forced" protonation of key residues. The full activation occurs only when all-trans-retinylidene assumes the most extended conformation and that the β-ionone ring of the chromophore can act on its protein environment. Although the mechanism of activation is still unclear, it is suspected that a profound relationship with another surprising observation, namely that the FTIR spectrum indicated an active species, whereas a spectral motif indicating protonation of the counterion Glu113 and salt bridge breaking was altered in its spectral properties.

The most obvious explanation for the pH-dependent activity would be that H+ adjusts the retinal binding site in a way that is partially photoactivatable and resembles a state generated during photoactivation of wild-type rhodopsin. Another non-exclusive explanation is that the restricted photochemistry of the 6-ring-retinals is sufficient to partially remove their reverse agonist-like property in a way that eventually allows protonation of key residue(s) (including Glu134) and the formation of the active conformation (similar to the opsin/opsin*equilibrium). 3) In native Meta II, the energy content is high enough to force the receptor into the active conformation, even at neutral and basic pH values. The apparent $pK_a$ of the light-induced active species of 11-cis-6-ring-Rh is 5.4, only one pH unit lower and thus approximately 1.5 kcal off the $pK_a$, of a free Glu residue, whereas the protonated species of Meta II has pKa of 6.7. Energy is required to protonate a residue at a pH higher than its native pKa of the observed active species in native and 11-cis-6-ring-retinal-regenerated rhodopsin.

In conclusion, it appears that the isomerization of retinal in the rhodopsin binding pocket of native or 6-locked retinals leads to conformational changes of the protein that allow coupling with Gt. Interestingly, this property is specific and even distinguishes between closely similar 6-ring- and 7-ring-containing retinals. This difference probably resides in the conformation of both retinals in the active site, their rigid nature imposed by the ring, and in the susceptibility of 6-ring-containing retinal to isomerization.

Use of 6- and 7-Ring-Containing Analogs in Leber Congenital Amaurosis:

Mutations in the RPE65 gene have been identified in patients diagnosed with Leber congenital amaurosis (LCA) (Leber, *Arch. Ophthalmol.* (*Paris*) 15:1-25 (1869); Marlhens et al., *Nat. Genet.* 17:139-41 (1997)), an autosomal recessive childhood-onset severe retinal dystrophy (Gu et al., *Nat. Genet.* 17:194-97 (1997)), and autosomal recessive retinitis pigmentosa (Morimura et al., *Proc. Natl. Acad. Sci. USA* 95:3088-93 (1998)). LCA is characterized by congenital blindness or by poor central vision, slight fundus changes, nearly absent electroretinogram signal, nystagmus, reduced papillary reactions, occasional photophobia (Schappert-Kimmijser et al., *Opthalmologica* 137:420-22 (1949)), eventual pigmentary degeneration of the retina, the absence of rod photoreceptors, remnants of cones, clumping of pigment in RPE. and an absence of chorioretinal adhesions (Leber, *Arch. Ophthalmol.* (*Paris*) 15:1-25 (1869): Kroll et al., *Arch. Ophthalmol.* 71:683-690 (1964)). The genetic abnormalities of LCA involve genes from different physiological pathways (Cremers et al., *Hum. Mol. Genet.* 11:1169-76 (2002)), and RPE65 gene mutations account for approximately 12% of all LCA cases (Thompson et al., *Invest. Ophthal. Vis. Sci.* 41:4293-99 (2000)).

Several therapeutic approaches to treating LCA have been proposed. These methods include RPE transplantation, gene replacement therapy, and pharmacological intervention. To date, most experimental therapeutical interventions for inherited degenerations in animals are aimed to slow down the progression of degeneration. Encouragingly, the block in the retinoid cycle caused by RPE65 gene mutations may be overcome pharmacologically by the oral addition of 9-cis-retinal, thereby creating iso-rhodopsin. Within 48 hours after cis-retinoid administration, rod photopigment was formed and rod physiology was improved dramatically, thus demonstrating that pharmacological intervention has the potential to restore vision when RPE65 is not present. This long term study on the effectiveness of the 9-cis-retinal intervention on restoration of visual function further lends support to this idea.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A method of treating Leber Congenital Amaurosis (LCA) in an LRAT-defective human subject having a mutation in the gene encoding the LRAT protein, comprising:
   administering a therapeutically effective amount of a 9-cis-retinal to the LRAT-defective human subject, wherein the LRAT-defective human subject has a deficiency of endogenous 11-cis-retinal in the eye and the 9-cis-retinal forms a functional opsin/chromophore complex in the eye.

2. The method of claim 1, wherein the 9-cis-retinal is administered locally to the eye of the human subject.

3. The method of claim 2, wherein the local administration is by eye drops, intraocular injection or periocular injection.

4. The method of claim 1 wherein the 9-cis-retinal is administered systemically by oral dosage form or injection.

5. A method of treating Leber Congenital Amaurosis (LCA) in an LRAT-defective human subject having a mutation in the gene encoding the LRAT protein, comprising:
   administering a therapeutically effective amount of 9-cis-retinal by local administration to an eye of the LRAT-defective human subject, wherein the LRAT-defective human subject has a deficiency of endogenous 11-cis-retinal in the eye and the 9-cis-retinal forms a functional opsin/chromophore complex in the eye.

6. The method of claim 5, wherein the local administration is by eye drops, intraocular injection or periocular injection.

* * * * *

UNITED STATES PATENT AND TRADEMARK OFFICE
CERTIFICATE OF CORRECTION

PATENT NO.         : 8,962,691 B2                                        Page 1 of 3
APPLICATION NO.    : 13/619607
DATED              : February 24, 2015
INVENTOR(S)        : Palczewski and Saperstein It is certified that error appears in the above-identified patent and that said Letters Patent is hereby corrected as shown below:

Title page under item (63): change "Continuation of application No. 13/420,465, filed on Mar. 14, 2012, which is a continuation of application No. 10/548,612, filed as application No. PCT/US2004/007937 on Mar. 15, 2004, now abandoned." to --Continuation of application No. 13/420,465, filed on Mar. 14, 2012, which is a continuation of application No. 10/548,612, filed September 7, 2005, now abandoned, which is a U.S. national phase application of international patent application No. PCT/US2004/007937, filed on Mar. 15, 2004.--

In the Specification

Column 1, line 49 through line 53: replace "Because the macula is the area which enables one to discern small details and to read or drive, its deterioration may bring about diminished visual acuity and even and to read or drive, its deterioration may bring about diminished visual acuity and even blindness." with --Because the macula is the area which enables one to discern small details and to read or drive, its deterioration may bring about diminished visual acuity and even blindness.--

Column 9, beginning on line 30 and ending on line 45: replace

"...the following formula III:

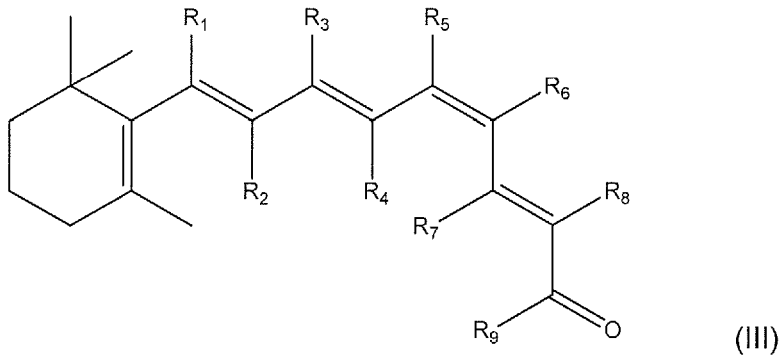

(III)

Signed and Sealed this
Twelfth Day of April, 2016

Michelle K. Lee
*Director of the United States Patent and Trademark Office*

CERTIFICATE OF CORRECTION (continued)
U.S. Pat. No. 8,962,691 B2

Each of R1 to R9 can be independently selected from hydrogen, alkyl, branched alkyl, cyclo-alkyl, halogen, a heteratom, or the like."

with --...the following formulas IIIa and IIIb:

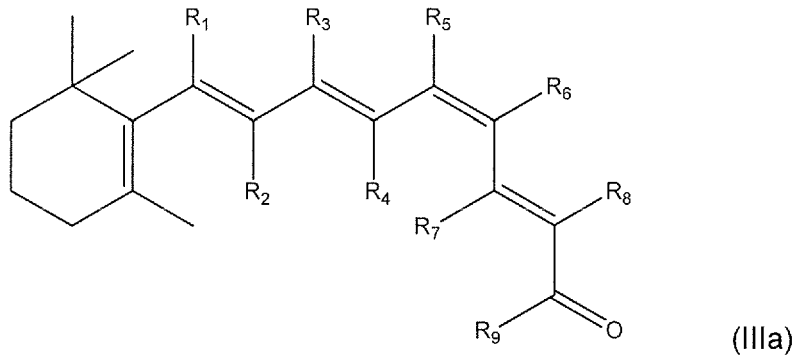

(IIIa)

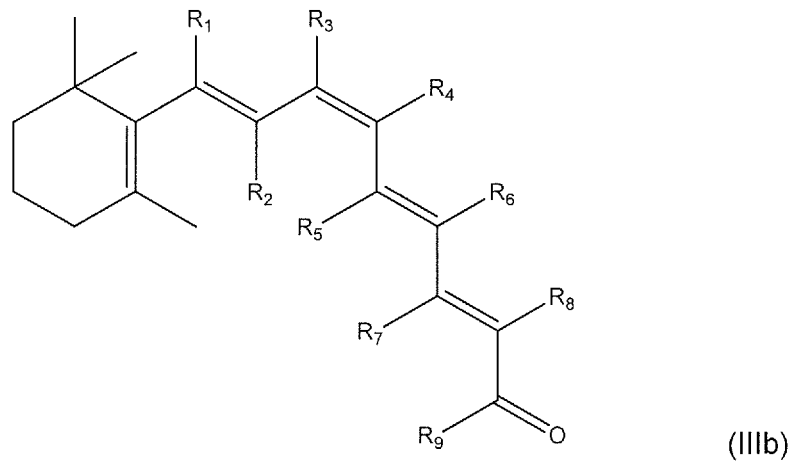

(IIIb)

Each of R1 to R9 can be independently selected from hydrogen, alkyl, branched alkyl, cyclo-alkyl, halogen, a heteroatom, or the like.--

Column 12, beginning on line 17 and ending on line 30: replace

"In yet another embodiment, the synthetic retinoid is of the following formula XIII.

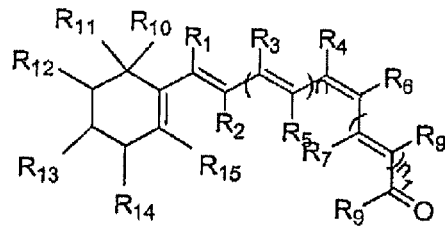

with --In yet another embodiment, the synthetic retinoid is of the following formula XIII.

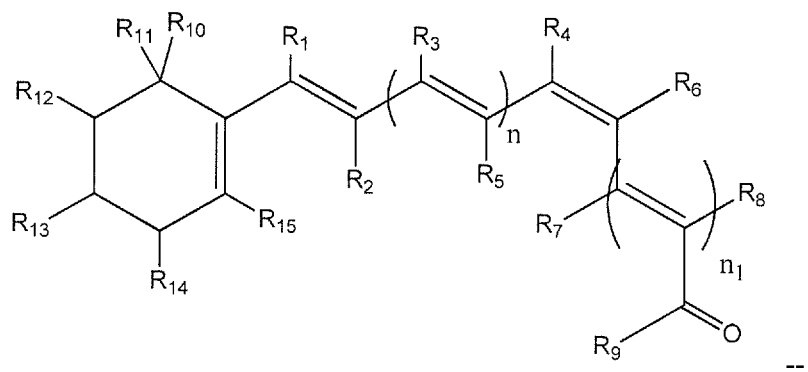
--